United States Patent
Liu et al.

(10) Patent No.: US 9,447,081 B2
(45) Date of Patent: Sep. 20, 2016

(54) SUBSTITUTED PYRIMIDINES AS PHARMACEUTICALS AND INSECTICIDES

(71) Applicant: SHENYANG SINOCHEM AGROCHEMICALS R&D CO., LTD., Shenyang (CN)

(72) Inventors: Changling Liu, Liaoning (CN); Aiying Guan, Liaoning (CN); Jie Lan, Liaoning (CN); Lizeng Wang, Liaoning (CN); Bin Wang, Liaoning (CN); Minna Zhu, Liaoning (CN); Qin Sun, Liaoning (CN); Weijing Ren, Liaoning (CN); Cong Feng, Liaoning (CN); Lanhui Ren, Liaoning (CN); Baoshan Chai, Liaoning (CN); Zhinian Li, Liaoning (CN)

(73) Assignee: SHENYANG SINOCHEM AGROCHEMICALS R&D CO., LTD., Shenyang, Liaoning (CN)

( * ) Notice: Subject to any disclaimer, the term of this patent is extended or adjusted under 35 U.S.C. 154(b) by 0 days.

(21) Appl. No.: 14/427,795

(22) PCT Filed: Oct. 24, 2013

(86) PCT No.: PCT/CN2013/085853
§ 371 (c)(1),
(2) Date: Mar. 12, 2015

(87) PCT Pub. No.: WO2014/063638
PCT Pub. Date: May 1, 2014

(65) Prior Publication Data
US 2015/0225378 A1    Aug. 13, 2015

(30) Foreign Application Priority Data

Oct. 25, 2012 (CN) .......................... 2012 1 0414006

(51) Int. Cl.

| | | |
|---|---|---|
| *A61K 31/506* | (2006.01) | |
| *C07D 239/42* | (2006.01) | |
| *C07D 317/50* | (2006.01) | |
| *C07D 405/12* | (2006.01) | |
| *C07D 405/14* | (2006.01) | |
| *A01N 43/54* | (2006.01) | |
| *C07D 409/14* | (2006.01) | |
| *C07D 417/14* | (2006.01) | |

(52) U.S. Cl.
CPC ............. *C07D 405/12* (2013.01); *A01N 43/54* (2013.01); *C07D 405/14* (2013.01); *C07D 409/14* (2013.01); *C07D 417/14* (2013.01)

(58) Field of Classification Search
CPC . A61K 31/506; C07D 239/42; C07D 317/50
USPC .......................... 514/256; 544/328; 549/434
See application file for complete search history.

(56) References Cited

U.S. PATENT DOCUMENTS

| | | | |
|---|---|---|---|
| 4,845,097 A | 7/1989 | Matsumoto et al. | |
| 4,977,264 A | 12/1990 | Mills et al. | |
| 4,985,426 A | 1/1991 | Yoshioka et al. | |
| 5,468,751 A | 11/1995 | Kristiansen et al. | |
| 5,925,644 A | 7/1999 | Jakobi et al. | |

(Continued)

FOREIGN PATENT DOCUMENTS

| | | |
|---|---|---|
| CN | 1312250 | 9/2001 |
| CN | 101938905 | 1/2011 |

(Continued)

OTHER PUBLICATIONS

Bniniecki, Stanislaw; Kolodynska, Zofia; Zlakowska, Wiedslawa. "Synteza 4- [β-3'-4'-Metylenodwuoksyfenylo)-Etyloamino]-Chinazoliny Oraz Produkty Kondensacji 4-Chlorochinazoly Z Uretanem Etylowym I Tiosynamina". ACTA Poloniae Pharmaceutica (1966), 23(1), 1-6.

(Continued)

*Primary Examiner* — Douglas M Willis
(74) *Attorney, Agent, or Firm* — Smith, Gambrell & Russell, LLP

(57) ABSTRACT

The invention discloses a homopiperony lamine compound which has a structural general formula I as follows as shown in the specification:

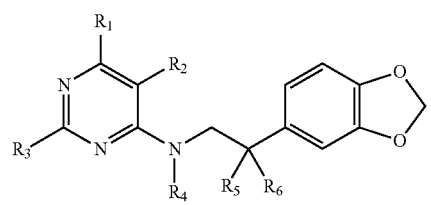

wherein definitions of substituents in the formula are as shown in the specification.

The compound shown as the general formula I has broad-spectrum bactericidal and insecticidal activity in the field of agriculture. The compound shown as the general formula I has a good prevention effect on various germs such as cucumber downy mildew, wheat powdery mildew, *puccinia sorghi*, rice blast and cucumber gray mold, and particularly, still has the good prevention and control effect on the cucumber downy mildew, the *puccinia sorghi* and the wheat powdery mildew at a lower dosage. At the same time, a part of compound has better insecticidal activity, and can be used for preventing and controlling various insect pests such as diamondback moths, *myzus persicae*, armyworms and *tetranychus cinabarinus* boisdu.

11 Claims, No Drawings

(56) References Cited

U.S. PATENT DOCUMENTS

| | | |
|---|---|---|
| 6,090,815 A | 7/2000 | Masuda et al. |
| 2004/0092402 A1 | 5/2004 | Kuragano et al. |

FOREIGN PATENT DOCUMENTS

| | | |
|---|---|---|
| DE | 19647317 | 5/1998 |
| EP | 0370704 | 5/1990 |
| EP | 0424125 | 4/1991 |
| EP | 0543402 | 5/1993 |
| JP | S54-2325 | 1/1979 |
| JP | S59-204177 | 11/1984 |
| JP | H07-070085 | 3/1995 |
| JP | H09-124613 | 5/1997 |
| JP | H10-36355 | 2/1998 |
| JP | 20000007662 | 1/2000 |
| JP | 2001504473 | 4/2001 |
| JP | 2004238380 | 8/2004 |
| JP | 2006008542 | 1/2006 |
| WO | 9822446 | 5/1998 |
| WO | 01/55143 | 8/2001 |
| WO | 02/094832 | 11/2002 |
| WO | 2004093800 | 11/2004 |
| WO | 2009/081112 | 7/2009 |
| ZA | 9710187 | 5/1998 |

OTHER PUBLICATIONS

Abstract of Nardi, D.; Marui, L; Barzaghi, F. "Antiocholesteremic substances—diphenyl ethers, diphenyl and dibenzyl derivatives." Farmaco, Edizione Scientifica (1965), 20(6), 456-62 (one page Abstract).

Rasmussen, C.A.H.; van Der Plas, H.C. "Aspects of the amination of 4-t-butyl-5-halogenopyrimidines by potassium amide in liquid ammonia". Recueil des Travaux Chimiques des Pays-Bas (1978), 97(11), pp. 288-292.

Whitehead, Calvert W. "Diuretics III. 4,6-Diaminopyrimidines", Journal of the American Chemical Society, 1958, 80, 2185-2189.

International Search Report for PCT/CN2013/085853 mailed Feb. 20, 2014.

SUBSTITUTED PYRIMIDINES AS PHARMACEUTICALS AND INSECTICIDES

FIELD OF THE INVENTION

The present invention relates to the fungicide and insecticide. Specifically to substituted pyrimidines and uses thereof.

BACKGROUND OF THE INVENTION

Homopiperonylbenzylamine compounds having following general formula and specific compound PC-1 were reported in Patent EP 424125A2, some compounds have some fungicidal and acricidal activities at the concentration of 50-500 ppm.

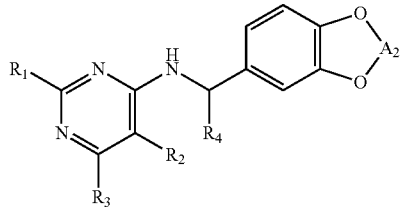

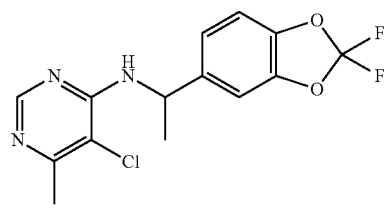

PC-1

The benzylamine compound containing benzoxazoly moiety as shown below was disclosed in patent WO 2001055143 applied as fungicide, insecticide and acricide:

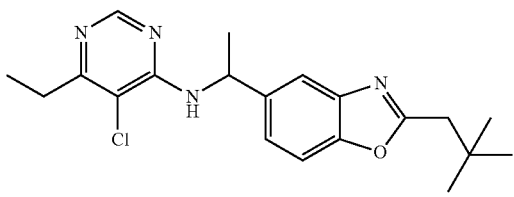 [SMILES: CCc1ncnc(NC(C)c2ccc3oc(CC(C)(C)C)nc3c2)c1Cl]

Patent WO 2002094832 published benzylamine compound having structural general formula as shown in the following and the specific compound:

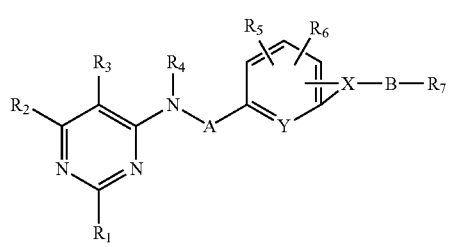

Patent EP 370704, EP 543402 and JP 07070085 published benzylamine compound having structural general formula as shown in the following and the specific compound:

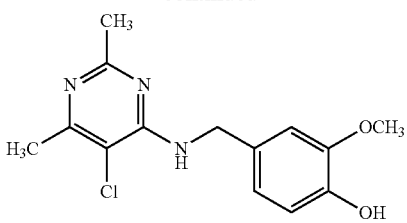

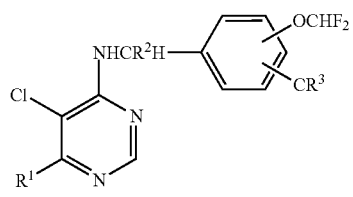

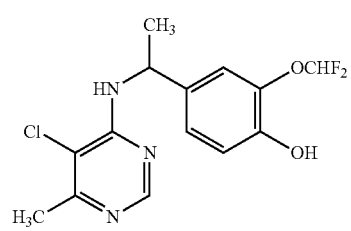

Patent WO2009081112A2 disclosed homopiperonylbenzylamine compound as shown below with application as herbicide:

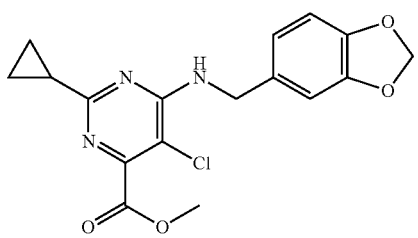 [SMILES: COC(=O)c1nc(C2CC2)nc(NCc2ccc3c(c2)OCO3)c1Cl]

The following ethylamine compounds having general formula and the preparation method of the specific compound were reported in patent JP 10036355:

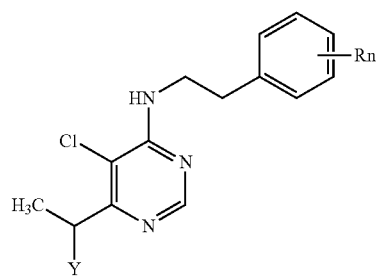

-continued

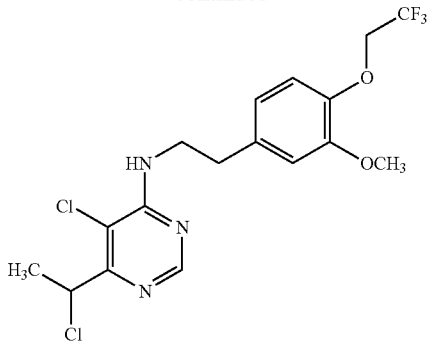

The following ethylamine compound was reported used as fungicide in patent JP54002325:

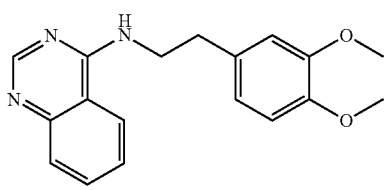 [SMILES: COc1ccc(CCNc2ncnc3ccccc23)cc1OC]

Acta Poloniae Pharmaceutica (1966), 23(1), 1-6 disclosed homopiperonylethylamine compound as shown below ACTA-1 applied as pharmaceutical:

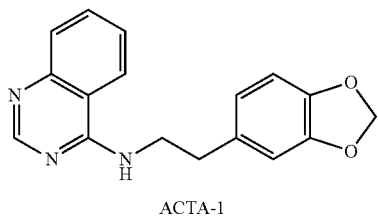 [SMILES: c1ccc2c(NCCc3ccc4c(c3)OCO4)ncnc2c1]

ACTA-1

In the prior art, although many homopiperonylbenzylamine, homopiperonylethylamine compounds somewhat similar to the structures in present invention, and benzylamine, ethylamine structures containing pyrimidinyl moiety, the substituted pyrimidines having general formula I of the present invention has not been reported.

SUMMARY OF THE INVENTION

New pesticides with novel structure and excellent property are needed by modern agricultural production. The object of the present invention is to provide a kind of homopiperonylethylamine to control a variety of plant pathogens/diseases and/or insects/mites at very low doses, which can be used to prepare substances to control pathogens and insects/mites in agriculture and other field.

Detailed description of the invention is as follows:

The present invention provides a homopiperonylethylamine compounds having general formula I:

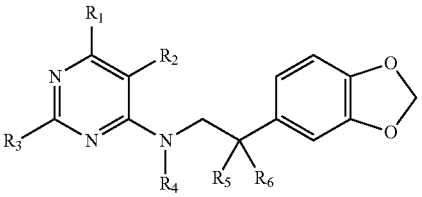

Wherein:

$R_1$ is selected from halo, $C_1$-$C_{12}$-alkyl, $C_3$-$C_{12}$-cycloalkyl, halo$C_1$-$C_{12}$alkyl, $C_1$-$C_{12}$alkoxy, halo$C_1$-$C_{12}$alkoxy, $C_3$-$C_{12}$alkenyloxy, halo$C_3$-$C_{12}$alkenyloxy, $C_3$-$C_{12}$alkynyloxy, halo$C_3$-$C_{12}$alkynyloxy, $C_1$-$C_{12}$alkylsulfonyloxy, $C_1$-$C_{12}$-alkylthio, $C_1$-$C_{12}$alkylsulfinyl, $C_1$-$C_{12}$alkylsulfonyl, COOH, $C_1$-$C_{12}$alkoxycarbonyl, CONH, $C_1$-$C_{12}$alkylaminocarbonyl, CONHCN, NHOCH$_3$, N(CH$_3$)NH$_2$, NHN(CH$_3$)$_2$, CONHCH$_2$CN, NH$_2$, $C_1$-$C_{12}$alkylamino, di($C_1$-$C_{12}$alkyl)amino, cyano$C_1$-$C_{12}$alkylamino, $C_1$-$C_{12}$alkylcarbonylamino, $C_1$-$C_{12}$alkoxycarbonylamino, $C_1$-$C_{12}$alkoxy$C_1$-$C_{12}$alkyl, $C_1$-$C_{12}$alkylthio$C_1$-$C_{12}$alkyl, $C_1$-$C_{12}$alkylsulfinyl$C_1$-$C_{12}$alkyl, $C_1$-$C_{12}$alkylsulfonyl$C_1$-$C_{12}$alkyl, hydroxyl$C_1$-$C_{12}$alkyl or $C_1$-$C_{12}$alkylcarbonyloxy$C_1$-$C_{12}$alkyl;

$R_2$ is selected from H, halo, CN, NO$_2$, $C_1$-$C_{12}$alkyl, $C_1$-$C_{12}$alkoxy or halo$C_1$-$C_{12}$alkoxy;

$R_3$ is selected from H, halo, $C_1$-$C_{12}$alkyl, $C_3$-$C_{12}$cycloalkyl, halo$C_1$-$C_{12}$alkyl, $C_1$-$C_{12}$alkylthio, $C_1$-$C_{12}$alkoxy or halo$C_1$-$C_{12}$alkoxy;

$R_4$ is selected from H, OH, C(=O)H, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_1$-$C_{12}$alkylthio, $C_2$-$C_{12}$alkenylthio, $C_2$-$C_{12}$alkenyl, $C_2$-$C_{12}$alkynyl, halo$C_2$-$C_{12}$alkenyl, halo$C_2$-$C_{12}$alkynyl, $C_1$-$C_{12}$alkoxy $C_1$-$C_{12}$alkyl, halo$C_1$-$C_{12}$alkoxy $C_1$-$C_{12}$alkyl, $C_1$-$C_{12}$alkylthio $C_1$-$C_{12}$alkyl, halo$C_1$-$C_{12}$alkylthio $C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylaminosulfonyl, di($C_1$-$C_{12}$alkyl)aminosulfonyl, $C_1$-$C_{12}$alkylsulfonylaminocarbonyl, $C_1$-$C_{12}$alkylcarbonylaminosulfonyl, $C_3$-$C_{12}$cycloalkyloxycarbonyl, $C_1$-$C_{12}$alkylcarbonyl, halo$C_1$-$C_{12}$alkylcarbonyl, $C_1$-$C_{12}$alkoxycarbonyl, halo$C_1$-$C_{12}$alkoxycarbonyl, $C_1$-$C_{12}$alkylcarbonyl$C_1$-$C_{12}$alkyl, $C_1$-$C_{12}$alkoxycarbonyl $C_1$-$C_{12}$alkyl, $C_1$-$C_{12}$alkylaminocarbonyl, di($C_1$-$C_{12}$alkyl)aminocarbonyl, $C_2$-$C_{12}$ alkenoxycarbonyl, $C_2$-$C_{12}$ alkynoxycarbonyl, $C_1$-$C_{12}$alkoxy $C_1$-$C_{12}$alkoxycarbonyl, $C_1$-$C_{12}$alkylaminothio, di($C_1$-$C_{12}$alkyl)aminothio, optionally substituted arylcarbonyl $C_1$-$C_6$alkyl, arylcarbonyl, aryloxycarbonyl, aryl$C_1$-$C_6$alkyloxycarbonyl, aryl$C_1$-$C_6$alkyl or heteroaryl $C_1$-$C_6$alkyl wherein substituents are independently selected from the group consisting of halo, NO$_2$, CN, $C_1$-$C_6$alkyl, halo$C_1$-$C_6$alkyl, $C_1$-$C_6$ alkoxy or halo$C_1$-$C_6$alkoxy;

$R_5$, $R_6$ are independently selected from H, $C_1$-$C_8$alkyl, $C_3$-$C_8$cycloalkyl, $C_2$-$C_8$alkenyl, $C_2$-$C_8$ alkynyl, halo$C_2$-$C_8$ alkenyl, halo$C_2$-$C_8$ alkynyl, $C_1$-$C_8$ alkoxy $C_1$-$C_8$alkyl, optionally substituted aryl$C_1$-$C_4$alkyl or heteroaryl $C_1$-$C_4$alkyl, wherein substituents are independently selected from the group consisting of halo, $C_1$-$C_4$alkyl, halo$C_1$-$C_4$alkyl, $C_1$-$C_4$ alkoxy or halo$C_1$-$C_4$ alkoxy;

or $R_5$ and $R_6$, together with the carbon to which they are attached, form a $C_3$-$C_8$ carbocycle;

or an agricultural or pharmaceutical salt thereof.

$R_5$, $R_6$ may be the same or different, selected respectively from H, $C_1$-$C_8$alkyl, $C_3$-$C_8$cycloalkyl, $C_2$-$C_8$ alkenyl, $C_2$-$C_8$ alkynyl, halo$C_2$-$C_8$alkenyl, halo$C_2$-$C_8$ alkynyl, $C_1$-$C_8$ alkoxy $C_1$-$C_8$alkyl, unsubstituted or further substituted aryl$C_1$-$C_4$alkyl or heteroaryl $C_1$-$C_4$alkyl by 1 to 3 following groups: halo, $C_1$-$C_4$alkyl, halo$C_1$-$C_4$alkyl; $C_1$-$C_4$ alkoxy or halo$C_1$-$C_4$ alkoxy;

$CR_5R_6$ can also form $C_3$-$C_8$ cycle;

Or the salts formed from the compounds of general formula I.

The preferred compounds of this invention are: In the general formula I $R_1$ is selected from halo, $C_1$-$C_8$alkyl, halo$C_1$-$C_8$ alkyl, $C_3$-$C_8$cycloalkyl, $C_1$-$C_8$alkoxy, halo$C_1$-$C_8$alkoxy, $C_3$-$C_8$ alkenyloxy, halo$C_3$-$C_8$ alkenyloxy, $C_3$-$C_8$ alkynyloxy, halo$C_3$-$C_8$ alkynyloxy, $C_1$-$C_8$ alkylsulfonyloxy, $C_1$-$C_8$ alkylthio, $C_1$-$C_8$ alkylsulfinyl, $C_1$-$C_8$ alkylsulfonyl, $NH_2$, $C_1$-$C_8$alkylamino, di($C_1$-$C_8$alkyl)amino, cyano$C_1$-$C_8$ alkylamino, $C_1$-$C_8$ alkylcarbonylamino, $C_1$-$C_8$ alkoxycarbonylamino, $C_1$-$C_8$ alkoxy$C_1$-$C_8$alkyl, $C_1$-$C_8$ alkylthio $C_1$-$C_8$alkyl, $C_1$-$C_8$ alkylsulfinyl $C_1$-$C_8$alkyl, $C_1$-$C_8$ alkylsulfonyl $C_1$-$C_8$ alkyl, hydroxy $C_1$-$C_8$ alkyl or $C_1$-$C_8$alkylcarbonyloxy$C_1$-$C_8$alkyl;

$R_2$ is selected from H, halo, CN, $NO_2$, $C_1$-$C_8$alkyl, $C_1$-$C_8$alkoxy or halo$C_1$-$C_8$alkoxy;

$R_3$ is selected from H, halo or $C_1$-$C_8$alkyl;

$R_4$ is selected from H, OH, C(=O)H, $C_1$-$C_8$alkyl, halo$C_1$-$C_8$alkyl, $C_1$-$C_8$alkoxy, halo$C_1$-$C_8$alkoxy, $C_3$-$C_8$cycloalkyl, $C_1$-$C_8$alkylthio, $C_2$-$C_8$alkenylthio, $C_2$-$C_8$alkenyl, $C_2$-$C_8$ alkynyl, halo$C_2$-$C_8$alkenyl, halo$C_2$-$C_8$alkynyl, $C_1$-$C_8$ alkoxy $C_1$-$C_8$alkyl, halo$C_1$-$C_8$ alkoxy $C_1$-$C_8$alkyl, $C_1$-$C_8$ alkylthio $C_1$-$C_8$alkyl, halo$C_1$-$C_8$ alkylthio $C_1$-$C_8$alkyl, $C_1$-$C_8$ alkylsulfinyl, halo$C_1$-$C_8$ alkylsulfinyl, $C_1$-$C_8$ alkylsulfonyl, halo$C_1$-$C_8$ alkylsulfonyl, $C_1$-$C_8$ alkylaminosulfonyl, di($C_1$-$C_8$ alkyl)aminosulfonyl, $C_1$-$C_8$ alkylsulfonylaminocarbonyl, $C_1$-$C_8$ alkylcarbonylaminosulfonyl, $C_3$-$C_8$ cycloalkyloxycarbonyl, $C_1$-$C_8$alkylcarbonyl, halo$C_1$-$C_8$alkylcarbonyl, $C_1$-$C_8$ alkoxycarbonyl, halo$C_1$-$C_8$ alkoxycarbonyl, $C_1$-$C_8$alkylcarbonyl$C_1$-$C_8$alkyl, $C_1$-$C_8$ alkoxycarbonyl $C_1$-$C_8$alkyl, $C_1$-$C_8$ alkylaminocarbonyl, di($C_1$-$C_8$ alkyl)aminocarbonyl, $C_2$-$C_8$ alkenoxycarbonyl, $C_2$-$C_8$ alkynoxycarbonyl, $C_1$-$C_8$ alkoxy $C_1$-$C_8$ alkoxycarbonyl, $C_1$-$C_8$ alkylaminothio, di($C_1$-$C_8$ alkyl)aminothio, optionally substituted arylcarbonyl $C_1$-$C_4$alkyl, arylcarbonyl, aryloxycarbonyl, aryl$C_1$-$C_6$alkyloxycarbonyl, aryl$C_1$-$C_6$alkyl or heteroaryl $C_1$-$C_6$alkyl, wherein substituents are independently selected from the group consisting of halo, $NO_2$, CN, $C_1$-$C_4$alkyl, halo$C_1$-$C_4$alkyl, $C_1$-$C_4$ alkoxy or halo$C_1$-$C_4$ alkoxy;

$R_5$, $R_6$ are independently selected respectively from H, $C_1$-$C_8$alkyl, $C_3$-$C_8$cycloalkyl, $C_2$-$C_8$ alkenyl, $C_2$-$C_8$ alkynyl, halo$C_2$-$C_8$ alkenyl, halo$C_2$-$C_8$ alkynyl, $C_1$-$C_8$alkoxy $C_1$-$C_8$alkyl, optionally substituted aryl$C_1$-$C_4$alkyl or heteroaryl $C_1$-$C_4$alkyl wherein substituents are independently selected from the group consisting of halo, $C_1$-$C_4$alkyl, halo$C_1$-$C_4$alkyl, $C_1$-$C_4$ alkoxy or halo$C_1$-$C_4$ alkoxy;

or $R_5$ and $R_6$, together with the carbon to which they are attached form a $C_3$-$C_8$ carbocycle;

or an agricultural or pharmaceutical salt thereof.

The further preferred compounds of this invention are: In the general formula I $R_1$ is selected from halo, $C_1$-$C_4$alkyl, halo$C_1$-$C_4$ alkyl, $C_3$-$C_6$cycloalkyl, $C_1$-$C_4$alkoxy, halo $C_1$-$C_4$alkoxy, $C_3$-$C_6$ alkenyloxy, halo$C_3$-$C_6$ alkenyloxy, $C_3$-$C_6$alkynyloxy, halo$C_3$-$C_6$alkynyloxy, $C_1$-$C_4$alkylsulfonyloxy, $C_1$-$C_4$alkylthio, $C_1$-$C_4$alkylsulfinyl, $C_1$-$C_4$ alkylsulfonyl, $NH_2$, $C_1$-$C_4$alkylamino, di($C_1$-$C_4$alkyl)amino, cyano $C_1$-$C_4$alkylamino, $C_1$-$C_4$alkylcarbonylamino, $C_1$-$C_4$alkoxycarbonylamino, $C_1$-$C_4$alkoxy $C_1$-$C_4$alkyl, $C_1$-$C_4$ alkylthio $C_1$-$C_4$alkyl, $C_1$-$C_4$alkylsulfinyl $C_1$-$C_4$alkyl, $C_1$-$C_4$alkylsulfonyl $C_1$-$C_4$alkyl, hydroxyl $C_1$-$C_4$alkyl or $C_1$-$C_4$alkylcarbonyloxy $C_1$-$C_4$alkyl;

$R_2$ is selected from H, halo, CN, $NO_2$, $C_1$-$C_4$alkyl, $C_1$-$C_4$alkoxy or halo $C_1$-$C_4$alkoxy;

$R_3$ is selected from H, halo or $C_1$-$C_4$alkyl;

$R_4$ is selected from H, OH, C(=O)H, $C_1$-$C_4$alkyl, halo $C_1$-$C_4$alkyl, $C_1$-$C_4$alkoxy, $C_2$-$C_4$alkenylthio, $C_3$-$C_6$cycloalkyl, $C_1$-$C_4$alkylthio, $C_2$-$C_4$alkenyl, $C_2$-$C_4$alkynyl, halo$C_2$-$C_4$alkenyl, halo$C_2$-$C_4$alkynyl, $C_1$-$C_4$ alkoxy $C_1$-$C_4$alkyl, halo $C_1$-$C_4$ alkoxy $C_1$-$C_4$alkyl, $C_1$-$C_4$alkylthio$C_1$-$C_4$alkyl, halo$C_1$-$C_4$alkylthio$C_1$-$C_4$alkyl, $C_1$-$C_4$alkylsulfinyl, halo $C_1$-$C_4$alkylsulfinyl, $C_1$-$C_4$alkylsulfonyl, halo $C_1$-$C_4$ alkylsulfonyl, $C_1$-$C_4$ alkylaminosulfonyl, di($C_1$-$C_4$ alkyl)aminosulfonyl, $C_1$-$C_4$ alkylsulfonylaminocarbonyl, $C_1$-$C_4$ alkylcarbonylaminosulfonyl, $C_3$-$C_6$ cycloalkyloxycarbonyl, $C_1$-$C_4$alkylcarbonyl, halo $C_1$-$C_4$alkylcarbonyl, $C_1$-$C_4$ alkoxycarbonyl, halo $C_1$-$C_4$ alkoxycarbonyl, $C_1$-$C_4$alkylcarbonyl $C_1$-$C_4$alkyl, $C_1$-$C_8$ alkoxycarbonyl $C_1$-$C_4$alkyl, $C_1$-$C_4$ alkylaminocarbonyl, di($C_1$-$C_4$alkyl)aminocarbonyl, $C_2$-$C_4$ alkenoxycarbonyl, $C_2$-$C_4$ alkynoxycarbonyl, $C_1$-$C_4$ alkoxy $C_1$-$C_4$alkoxycarbonyl, $C_1$-$C_4$ alkylaminothio, di($C_1$-$C_4$ alkyl)aminothio, optionally substituted arylcarbonyl $C_1$-$C_4$alkyl, arylcarbonyl, aryloxycarbonyl, aryl$C_1$-$C_4$alkyloxycarbonyl, aryl$C_1$-$C_4$alkyl or heteroaryl $C_1$-$C_4$alkyl, wherein substituents are independently selected from the group consisting of halo, $NO_2$, CN, $C_1$-$C_4$alkyl, halo$C_1$-$C_4$alkyl, $C_1$-$C_4$ alkoxy or halo$C_1$-$C_4$ alkoxy;

$R_5$, $R_6$ are independently selected respectively from H, $C_1$-$C_4$alkyl, $C_3$-$C_6$cycloalkyl, $C_2$-$C_4$ alkenyl, $C_2$-$C_4$ alkynyl, halo$C_2$-$C_4$ alkenyl, halo$C_2$-$C_4$ alkynyl, $C_1$-$C_4$ alkoxy $C_1$-$C_4$alkyl, optionally substituted aryl$C_1$-$C_4$alkyl or heteroaryl $C_1$-$C_4$alkyl, wherein substituents are independently selected from the group consisting of halo, $C_1$-$C_4$alkyl, halo$C_1$-$C_4$alkyl, $C_1$-$C_4$ alkoxy or halo$C_1$-$C_4$ alkoxy;

or $R_5$ and $R_6$, together with the carbon to which the are attached, form a $C_3$-$C_8$ carbocycle;

or an agricultural or pharmaceutical salt thereof selected from the group consisting of hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid and citric acid.

The further preferred compounds of this invention are: In the general formula I $R_1$ is selected from halo, $C_1$-$C_4$alkyl, $CF_3$, $CHF_2$, $CCl_3$, $CHCl_2$, $C_3$-$C_6$cycloalkyl, $C_1$-$C_4$alkoxy, halo $C_1$-$C_4$alkoxy, $C_1$-$C_4$alkylthio, $C_1$-$C_4$alkylsulfinyl, $C_1$-$C_4$ alkylsulfonyl, $C_1$-$C_4$alkoxy$C_1$-$C_4$alkyl or $C_1$-$C_4$ alkylthio $C_1$-$C_4$alkyl;

$R_2$ is selected from H, halo, CN, $NO_2$, $C_1$-$C_4$alkyl, $C_1$-$C_4$alkoxy or halo $C_1$-$C_4$alkoxy;

$R_3$ is selected from H or $C_1$-$C_4$alkyl:

$R_4$ is selected from H, C(=O)H, $C_1$-$C_4$alkyl, $C_3$-$C_6$cycloalkyl, optionally substituted arylcarbonyl $C_1$-$C_4$alkyl, arylcarbonyl, aryloxycarbonyl, aryl$C_1$-$C_4$alkyloxycarbonyl, aryl$C_1$-$C_4$alkyl or heteroaryl $C_1$-$C_4$alkyl, wherein substituents are independently selected from the group consisting of halo, $NO_2$, CN, $C_1$-$C_4$alkyl, halo$C_1$-$C_4$alkyl, $C_1$-$C_4$ alkoxy or halo$C_1$-$C_4$ alkoxy;

$R_5$, $R_6$ are independently selected respectively from H or $C_1$-$C_4$alkyl;

or an agricultural or pharmaceutical salt thereof selected from the group consisting of hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid and citric acid.

The further preferred compounds of this invention are: In the general formula I $R_1$ is selected from halo, $C_1$-$C_4$alkyl, $C_3$-$C_6$cycloalkyl, $CF_3$ or $CHF_2$;

$R_2$ is selected from H, halo, CN, $NO_2$ or $C_1$-$C_4$alkyl;

$R_3$ is H;

$R_4$ is H;

$R_5$, $R_6$ are selected respectively from H, $CH_3$ or $C_2H_5$;

or an agricultural or pharmaceutical salt thereof selected from the group consisting of hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid and citric acid.

The further preferred compounds of this invention are: In the general formula I $R_1$ is selected from F, Cl, Br, $CH_3$, $C_2H_5$, n-$C_3H_7$, i-$C_3H_7$, n-$C_4H_9$, i-$C_4H_9$, t-$C_4H_9$, cyclopropyl, $CF_3$ or $CHF_2$;

$R_2$ is Cl;

$R_3$ is H;

$R_4$ is H;

$R_5$, $R_6$ are selected respectively from H, $CH_3$ or $C_2H_5$;

or an agricultural or pharmaceutical salt thereof selected from the group consisting of hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid and citric acid.

The most preferred compounds of this invention are: In the general formula I $R_1$ is selected from Cl, $CH_3$, $C_2H_5$, $CF_3$ or $CHF_2$;

$R_2$ is Cl;

$R_3$ is H;

$R_4$ is H;

$R_5$ is H; and $R_6$ is H;

or an agricultural or pharmaceutical salt thereof selected from the group consisting of hydrochloric acid, sulfuric acid, phosphoric acid, trifluoroacetic acid, methylsulfonic acid and p-toluenesulfonic acid.

The terms used above to definite the compounds of general formula I represent substitutes as follow:

The "halogen" or "halo" is fluorine, chlorine, bromine or iodine.

The "alkyl" stands for straight or branched chain alkyl, such as methyl, ethyl, propyl, isopropyl or tert-butyl.

The "cycloalkyl" is substituted or unsubstituted cyclic alkyl, such as cyclopropyl, cyclopentyl or cyclohexyl. The substitute(s) is(are) methyl, halogen, etc.

The "haloalkyl" stands for straight or branched chain alkyl, in which hydrogen atoms can be all or partly substituted with halogen, such as chloromethyl, dichloromethyl, trichloromethyl, fluoromethyl, difluoromethyl, trifluoromethyl, etc.

The "alkoxy" refers to straight or branched chain alkyl, which is linked to the structure by oxygen atom.

The "alkenylthio" refers to straight or branched chain alkenyl, which is linked to the structure by sulfur atom. Such as $CH_2$=$CHCH_2S$—.

The "haloalkoxy" refers to straight or branched chain alkoxy, in which hydrogen atoms may be all or partly substituted with halogen, such as chloromethoxy, dichloromethoxy, trichloromethoxy, fluoromethoxy, difluoromethoxy, trifluoromethoxy, chlorofluoromethoxy, trifluoroethoxy, etc. The "alkylthio" refers to straight or branched chain alkyl, which is linked to the structure by sulfur atom.

The "alkenyl" refers to straight or branched chain alkenyl, such as ethenyl, 1-propenyl, 2-propenyl and different isomer of butenyl, pentenyl and hexenyl. Alkenyl also includes polyene, such as propa-1,2-dienyl and hexa-2,4-dienyl. The "haloalkenyl" stands for straight or branched chain alkenyl, in which hydrogen atoms can be all or partly substituted with halogen. The "alkynyl" refers to straight or branched chain alkynyl, such as ethynyl, 1-propynyl, 2-propynyl and different isomer of butynyl, pentynyl and hexynyl. Alkynyl also includes groups including more than one triple bonds, such as hexa-2,5-diynyl. The "haloalkynyl" stands for straight or branched chain alkynyl, in which hydrogen atoms can be all or partly substituted with halogen.

The alkenoxyl refers to straight or branched chain alkynes is linked to the structure by oxygen, The haloalkenoxyl stands for a straight-chain or branched alkenoxyl, in which hydrogen atoms may be all or partly substituted with halogen. The alkynoxyl refers to straight or branched chain alkynes is linked to the structure by oxygen. The haloalkynoxyl stands for a straight-chain or branched alkynoxyl, in which hydrogen atoms may be all or partly substituted with halogen.

The "alkylamino" refers to straight or branched chain alkyl, which is linked to the structure by nitrogen atom. The "cyanoalkylamino" refers to alkylamino, in which hydrogen atoms may be all or partly substituted with cyano, such as $CNCH_2NH$—, $CNCH_2CH_2NH$—.

The "alkylsulfinyl" means a straight-chain or branched alkyl is linked to the structure by (—SO—), such as methylsulfinyl.

The "haloalkylsulfinyl" stands for a straight-chain or branched alkylsulfinyl, in which hydrogen atoms may be all or partly substituted with halogen.

The "alkylsulfonyl" means a straight-chain or branched alkyl is linked to the structure by (—$SO_2$—), such as methylsulfonyl.

The "haloalkylsulfonyl" stands for a straight-chain or branched alkylsulfonyl, in which hydrogen atoms may be all or partly substituted with halogen.

The "alkylaminosulfonyl" refers to alkyl-NH—$SO_2$—. The "dialkylaminosulfonyl" refers to (alkyl)$_2$-NH—$SO_2$—. The "alkylsulfonylaminocarbonyl" refers to alkyl-$SO_2$—NH—CO—. The "alkylcarbonylaminosulfonyl" refers to alkyl-CO—NH—$SO_2$—. The "alkylcarbonyl" means alkyl is linked to the structure by carbonyl, such as $CH_3CO$—, $CH_3CH_2CO$—. The "haloalkylcarbonyl" stands for a straight-chain or branched alkylcarbonyl, in which hydrogen atoms may be all or partly substituted with halogen, such as $CF_3CO$—.

The "alkylcarbonylalkyl" refers to alkyl-CO-alkyl-. The "alkylcarbonylamino" such as $CH_3CONH$—, $CH_3CH_2NHCONH$—. The "alkylsulfonyloxy" means alkyl-$S(O)_2$—O—. The "alkoxycarbonyl" means alkyl-O—CO—, such as $CH_3OCO$—, $C_2H_5OCO$—. The "cycloalkyloxycarbonyl" means cyclopropyloxycarbonyl, cyclohexyloxycarbonyl. The "haloalkoxycarbonyl" means alkoxycarbonyl, in which hydrogen atoms can be all or partly substituted with halogen, such as $ClCH_2CH_2OCO$—, $CF_3CH_2OCO$—.

The "alkenoxycarbonyl" means $CH_2$=$CHCH_2OCO$—. The "alkynoxycarbonyl" means CH≡$CCH_2OCO$—. The "alkoxyalkoxycarbonyl" stands for $CH_3OCH_2CH_2OCO$—. The "alkylaminothio" refers to $CH_3NHS$—, $C_2H_5NHS$—. The "dialkylaminothio" refers to $(CH_3)_2NS$—, $(C_2H_5)_2NS$—. The "alkoxycarbonylalkyl" refers to alkyl-O—CO-alkyl, such as $CH_3OCOCH_2$—. The "alkoxycarbonylamino" refers to alkyl-O—CO—NH. The "alkoxyalkyl" means alkyl-O-alkyl-, such as CH₃OCH₂—. The "alkylthioalkyl" means alkyl-S-alkyl-, such as CH₃SCH₂—. The "haloalkoxyalkyl" refers to alkoxyalkyl, in which hydrogen atom may be all or partly substituted with halogen, such as ClCH2CH2OCH2-, CF3CH2OCH2-. The "halo alkylthioalkyl" refers to alkylthioalkyl, in which hydrogen atom may be all or partly substituted with halogen, such as ClCH₂CH₂SCH₂—, CF₃CH₂SCH₂—. The "alkylaminocarbonyl" means alkyl-NH—CO—, such as CH₃NHCO—, C₂H₅NHCO—. The "dialkylaminocarbonyl" means (alkyl)₂-NH—CO—, such as (CH₃)₂—N—CO—, (C₂H₅)₂—N—CO—. The "hydroxylalkyl" refers to HOCH₂—. The "alkylcarbonyloxyalkyl" such as CH₃COOCH₂—.

The "aryl" in arylalkyl, arylcarbonyl, arylcarbonylalkyl, aryloxycarbonyl and arylalkyloxycarbonyl includes phenyl or naphthyl etc. The "heteroaryl" in heteroarylalkyl stands for five member ring or six member ring containing one or more N, O, S hetero atoms, such as furyl, pyrazolyl, thiazolyl, pyridinyl, pyrimidinyl, pyrazinyl, pyridazinyl, triazinyl, quinolinyl, etc. Arylalkyl means benzyl, phenylethyl, 4-Cl-benzyl, etc. The heteroarylalkyl such as

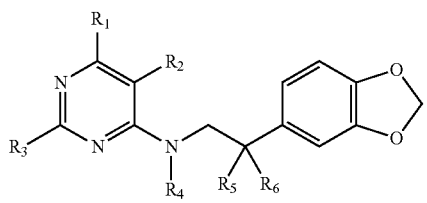

etc.

Arylcarbonyl refers to benzoyl, 4-Cl-benzoyl, etc. Arylcarbonylalkyl refers to PhCOCH₂—, etc.

Aryloxycarbonyl such as phenoxycarbonyl, p-chlorophenoxycarbonyl, p-nitrophenoxycarbonyl, naphthyloxycarbonyl, etc.

Arylalkyloxycarbonyl means benzyloxycarbonyl, p-chlorobenzyloxycarbonyl, p-trifluoromethylbenzyloxycarbonyl, etc.

In the general formula I, part of preferred substituents of $R_1$, $R_2$, $R_3$, $R_4$, $R_5$ and $R_6$ are separately listed in table 1 to table 5, but without being restricted thereby.

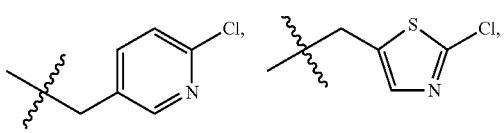

I

TABLE 1

| $R_1$ substituents | | | |
|---|---|---|---|
| $R_1$ | $R_1$ | $R_1$ | $R_1$ |
| F | CHF₂ | SCH₃ | NHOCH₃ |
| Cl | CHBr₂ | SOCH₃ | NHOC₂H₅ |
| Br | CF₃ | SO₂CH₃ | NHCOCH₃ |
| I | CH(CH₃)F | COOH | NHCOC₂H₅ |
| CH₃ | CH(CH₃)Cl | COOCH₃ | NHCOOCH₃ |
| C₂H₅ | CH(CH₃)Br | COOC₂H₅ | NHCOOC₂H₅ |

TABLE 1-continued

| $R_1$ substituents | | | |
|---|---|---|---|
| $R_1$ | $R_1$ | $R_1$ | $R_1$ |
| n-C₃H₇ | CH(n-C₄H₉)F | CONH₂ | N(CH₃)NH2 |
| i-C₃H₇ | CH(CH₃)₂F | CONHCH₃ | NHN(CH₃)₂ |
| n-C₄H₉ | OCH₃ | CONHCN | CH₂OCH₃ |
| i-C₄H₉ | OC₂H₅ | CONHCH₂CN | CH₂OCH₂CH₃ |
| t-C₄H₉ | OCF₃ | CON(CH₃)₂ | CH₂CH₂OCH₃ |
| cyclopropyl | OCH₂CH=CH₂ | NH₂ | CH₂CH₂OCH₂CH₃ |
| cyclopentyl | OCH₂CH=CHCl | NHCH₃ | CH(CH₃)SCH₃ |
| cyclohexyl | OCH₂C≡CH | NHC₂H₅ | CH(CH₃)SOCH₃ |
| CH₂Cl | OCH₂C≡C—I | N(CH₃)₂ | CH(CH₃)SO₂CH₃ |
| CHCl₂ | OCH₂C≡CCH₃ | N(C₂H₅)₂ | CH(CH₃)OH |
| CCl₃ | OSO₂CH₃ | NHCH₂CN | CH(CH₃)OCOCH₃ |

TABLE 2

| $R_2$ substituents | | | |
|---|---|---|---|
| $R_2$ | $R_2$ | $R_2$ | $R_2$ |
| H | NO₂ | t-C₄H₉ | OC₄H₉-i |
| F | CH₃ | OCH₃ | OC₄H₉-t |
| Cl | C₂H₅ | OC₂H₅ | OCH₂F |
| Br | n-C₃H₇ | OC₃H₇-n | OCHF₂ |
| I | i-C₃H₇ | OC₃H₇-i | OCF₃ |
| CN | n-C₄H₉ | OC₄H₉-n | OCH₂CF₃ |

TABLE 3

| $R_3$ substituents | | | | |
|---|---|---|---|---|
| $R_3$ | $R_3$ | $R_3$ | $R_3$ | $R_3$ |
| H | i-C₃H₇ | CHF₂ | OCH₃ | OCH₂CF₃ |
| F | n-C₄H₉ | CHBr₂ | OC₂H₅ | SCH₃ |
| Cl | t-C₄H₉ | CF₃ | OC₃H₇-n | SC₂H₅ |
| Br | cyclopropyl | CH(CH₃)F | OC₃H₇-i | SC₃H₇-n |
| I | cyclopentyl | CH(CH₃)Cl | OC₄H₉-n | SC₃H₇-i |
| CH₃ | cyclohexyl | CH(CH₃)Br | OC₄H₉-i | SC₄H₉-n |
| C₂H₅ | CHCl₂ | CH(n-C₄H₉)F | OC₄H₉-t | SC₄H₉-i |
| n-C₃H₇ | CCl₃ | CH(CH₃)₂F | OCF₃ | SC₄H₉-t |

TABLE 4

R4 substituents

| R4 | R4 | R4 | R4 |
|---|---|---|---|
| H | OH | —C(=O)H | CBr$_3$ |
| CH$_3$ | C$_2$H$_5$ | n-C$_3$H$_7$ | i-C$_3$H$_7$ |
| n-C$_4$H$_9$ | i-C$_4$H$_9$ | t-C$_4$H$_9$ | CCl$_3$ |
| CH$_2$Br | CHF$_2$ | CHBr$_2$ | CF$_3$ |
| CH$_2$Cl | CHCl$_2$ | CCl$_3$ | CH$_2$F |
| OCH$_3$ | OC$_2$H$_5$ | OCH(CH$_3$)$_2$ | OC(CH$_3$)$_3$ |
| OCF$_3$ | OCH$_2$CF$_3$ | OCH$_2$F | OCHF$_2$ |
| SCH$_3$ | SC$_2$H$_5$ | SCH$_2$CH=CH$_2$ | CH=CH$_2$ |
| CH$_2$CH=CH$_2$ | CH$_2$CH=CCl$_2$ | C≡CH | CH$_2$C≡CH |
| CH$_2$C≡C—I | CH$_2$OCH$_3$ | CH$_2$OCH$_2$CH$_3$ | CH$_2$CH$_2$OCH$_3$ |
| CH$_2$CH$_2$OCH$_2$CH$_3$ | CH$_2$OCH$_2$Cl | CH$_2$OCH$_2$CH$_2$Cl | CH$_2$CH$_2$OCH$_2$Cl |
| CH$_2$SCH$_3$ | CH$_2$SCH$_2$CH$_3$ | CH$_2$CH$_2$SCH$_3$ | CH$_2$CH$_2$SCH$_2$CH$_3$ |
| CH$_2$SCH$_2$Cl | CH$_2$SCH$_2$CH$_2$Cl | CH$_2$CH$_2$SCH$_2$Cl | SOCH$_3$ |
| SOC$_2$H$_5$ | SOCF$_3$ | SOCH$_2$CF$_3$ | SO$_2$CH$_3$ |
| SO$_2$C$_2$H$_5$ | SO$_2$CF$_3$ | SO$_2$CH$_2$CF$_3$ | SO$_2$NHCOCH$_3$ |
| SO$_2$NHCH$_3$ | SO$_2$N(CH$_3$)$_3$ | CONHSO$_2$CH$_3$ | COCH$_3$ |
| COC$_2$H$_5$ | CO-n-C$_3$H$_7$ | CO-i-C$_3$H$_7$ | CO-n-C$_4$H$_9$ |
| CO-i-C$_4$H$_9$ | CO-t-C$_4$H$_9$ | COCF$_3$ | COCH$_2$Cl |
| COOCH$_3$ | COOC$_2$H$_5$ | COO-n-C$_3$H$_7$ | COO-t-C$_4$H$_9$ |
| COOCF$_3$ | COOCH$_2$CH$_2$Cl | COOCH$_2$CF$_3$ | CH$_2$COOCH$_3$ |
| CH$_2$COOC$_2$H$_5$ | CH$_2$COCH$_3$ | CH$_2$COC$_2$H$_5$ | CONHCH$_3$ |
| CONHC$_2$H$_5$ | CONH-t-C$_4$H$_9$ | CON(CH$_3$)$_2$ | CON(C$_2$H$_5$)$_2$ |
| COOCH$_2$CH=CH$_2$ | COOCH$_2$C≡CH | COOCH$_2$OCH$_3$ | COOCH$_2$CH$_2$OCH$_3$ |
| SNHCH$_3$ | SNHC$_2$H$_5$ | SN(CH$_3$)$_2$ | SN(C$_2$H$_5$)$_2$ |

TABLE 4-continued
R₄ substituents
| $R_4$ | $R_4$ | $R_4$ | $R_4$ |
|---|---|---|---|
| 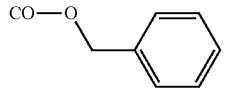 | 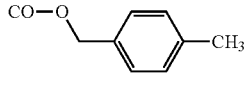 | 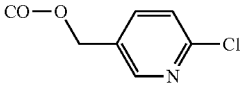 | 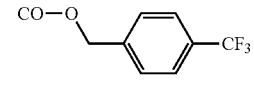 |
| 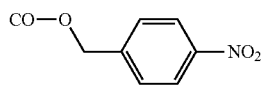 | 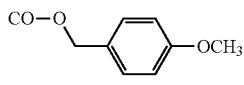 | 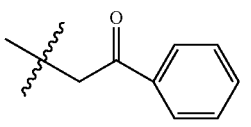 [SMILES: *CC(=O)c1ccccc1] | 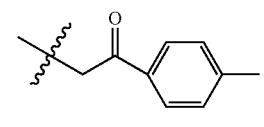 [SMILES: *CC(=O)c1ccc(C)cc1] |
| 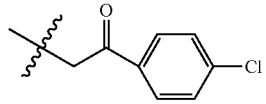 [SMILES: *CC(=O)c1ccc(Cl)cc1] | 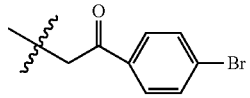 [SMILES: *CC(=O)c1ccc(Br)cc1] | 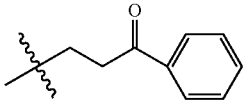 [SMILES: *CCC(=O)c1ccccc1] | 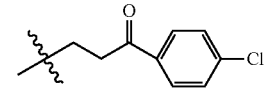 [SMILES: *CCC(=O)c1ccc(Cl)cc1] |
TABLE 5
$R_5(R_6)$ substituents
| $R_5(R_6)$ | $R_5(R_6)$ | $R_5(R_6)$ | $R_5(R_6)$ |
|---|---|---|---|
| H | 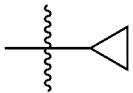 [SMILES: *C1CC1] | $CH_2C\equiv CH$ | 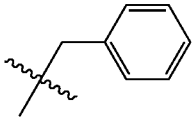 [SMILES: *Cc1ccccc1] |
| $CH_3$ | 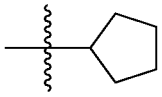 [SMILES: *C1CCCC1] | $CH_2CH=CCl_2$ | 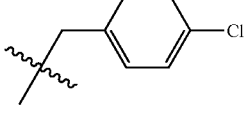 |
| $C_2H_5$ | 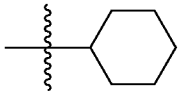 | $CH_2C\equiv C-I$ | 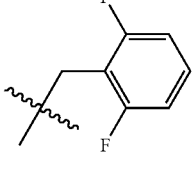 |
| n-$C_3H_7$ | t-$C_4H_9$ | $CH_2OCH_3$ | 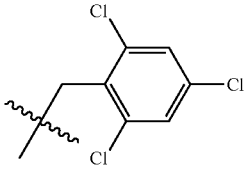 [SMILES: *Cc1c(Cl)cc(Cl)cc1Cl] |
| i-$C_3H_7$ | $CH=CH_2$ | $CH_2OCH_2CH_3$ | 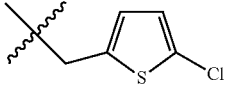 |
| n-$C_4H_9$ | $C\equiv CH$ | $CH_2CH_2OCH_3$ | 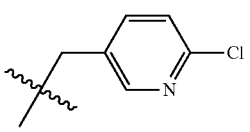 [SMILES: *Cc1ccc(Cl)nc1] |
| i-$C_4H_9$ | $CH_2CH=CH_2$ | $CH_2CH_2OCH_2CH_3$ | |

TABLE 5-continued

| $CR_5R_6$ |
|---|
| 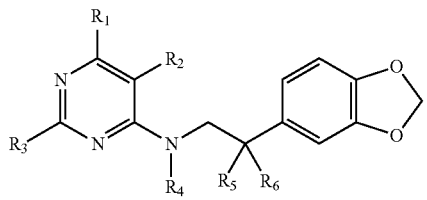 |

The present invention is also explained by the following compounds listed in Table 6 to Table 23, but without being restricted thereby.

I

R_1, R_2, R_3, R_4, R_5, R_6 structure (pyrimidine with benzodioxole group)

Table 6: in general formula I, $R_2$=Cl, $R_3$=$R_4$=$R_5$=$R_6$=H, the substituent $R_1$ refers to Table 6, the representative compounds are coded as 1-65.

TABLE 6

| No. | $R_1$ |
|---|---|
| 1 | F |
| 2 | Cl |
| 3 | Br |
| 4 | I |
| 5 | $CH_3$ |
| 6 | $C_2H_5$ |
| 7 | $n-C_3H_7$ |
| 8 | $i-C_3H_7$ |
| 9 | $n-C_4H_9$ |
| 10 | $i-C_4H_9$ |
| 11 | $t-C_4H_9$ |
| 12 | 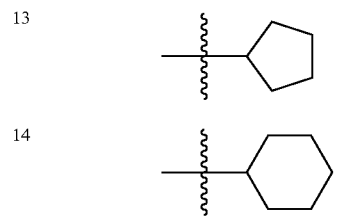 |
| 13 | (cyclopentyl) |
| 14 | (cyclohexyl) |
| 15 | $CH_2Cl$ |
| 16 | $CHCl_2$ |
| 17 | $CCl_3$ |
| 18 | $CHF_2$ |
| 19 | $CHBr_2$ |
| 20 | $CF_3$ |
| 21 | $CH(CH_3)F$ |
| 22 | $CH(CH_3)Cl$ |
| 23 | $CH(CH_3)Br$ |
| 24 | $CH(CH_3)_2F$ |
| 25 | $OCH_2CH=CH_2$ |
| 26 | $OCH_2CH=CHCl$ |
| 27 | $OCH_2C\equiv CH$ |
| 28 | $OCH_2C\equiv C-I$ |
| 29 | $OCH_2C\equiv CCH_3$ |

TABLE 6-continued

| No. | $R_1$ |
|---|---|
| 30 | $OSO_2CH_3$ |
| 31 | $OCH_3$ |
| 32 | $OC_2H_5$ |
| 33 | $OCH_2F$ |
| 34 | $OCF_3$ |
| 35 | $SCH_3$ |
| 36 | $SOCH_3$ |
| 37 | $SO_2CH_3$ |
| 38 | COOH |
| 39 | $COOCH_3$ |
| 40 | $COOC_2H_5$ |
| 41 | $CONH_2$ |
| 42 | $CONHCH_3$ |
| 43 | CONHCN |
| 44 | $CONHCH_2CN$ |
| 45 | $CON(CH_3)_2$ |
| 46 | $NH_2$ |
| 47 | $NHCH_3$ |
| 48 | $NHC_2H_5$ |
| 49 | $N(CH_3)_2$ |
| 50 | $N(C_2H_5)_2$ |
| 51 | $NHCH_2CN$ |
| 52 | $NHOCH_3$ |
| 53 | $NHCOCH_3$ |
| 54 | $NHCOOC_2H_5$ |
| 55 | $N(CH_3)NH2$ |
| 56 | $NHN(CH_3)_2$ |
| 57 | $CH_2OCH_3$ |
| 58 | $CH_2OCH_2CH_3$ |
| 59 | $CH_2CH_2OCH_3$ |
| 60 | $CH_2CH_2OCH_2CH_3$ |
| 61 | $CH(CH_3)SCH_3$ |
| 62 | $CH(CH_3)SOCH_3$ |
| 63 | $CH(CH_3)SO_2CH_3$ |
| 64 | $CH(CH_3)OH$ |
| 65 | $CH(CH_3)OCOCH_3$ |

Table 7: in general formula I, $R_2$=Cl, $R_3$=Cl, $R_4$=$R_5$=$R_6$=H, the substituent $R_3$ is consistent with those in Table 6 and corresponding to 1-65 in table 6 in turn, the representative compounds are coded as 66-130.

Table 8: in general formula I, $R_2$=Cl, $R_3$=$CH_3$, $R_4$=$R_5$=$R_6$=H, the substituent $R_1$ is consistent with those in Table 6 and corresponding to 1-65 in table 6 in turn, the representative compounds are coded as 131-195.

Table 9: in general formula I, $R_2$=Cl, $R_3$ = 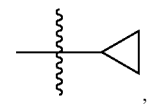, $R_4$=$R_5$=$R_6$=H, the substituent $R_1$ is consistent with those in Table 6 and corresponding to 1-65 in table 6 in turn, the representative compounds are coded as 196-260.

Table 10: in general formula I, R$_2$=Cl,

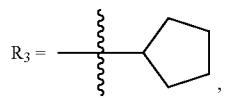

R$_4$=R$_5$=R$_6$=H, the substituent R$_1$ is consistent with those in Table 6 and corresponding to 1-65 in table 6 in turn, the representative compounds are coded as 261-325.

Table 11: in general formula I, R$_2$=Cl,

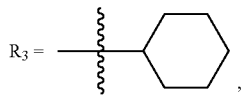

R$_4$=R$_5$=R$_6$=H, the substituent R$_1$ is e consistent with those in Table 6 and corresponding to 1-65 in table 6 in turn, the representative compounds are coded as 326-390.

Table 12: in general formula I, R$_2$=Cl, R$_3$=R$_4$=R$_5$=H, R$_6$=CH$_3$, the substituent R$_1$ is consistent with those in Table 6 and corresponding to 1-65 in table 6 in turn, the representative compounds are coded as 391-455, Table 13: in general formula I, R$_2$=Cl, R$_3$=Cl, R$_4$=R$_5$=H, R$_6$=CH$_3$, the substituent R$_1$ is consistent with those in Table 6 and corresponding to 1-65 in table 6 in turn, the representative compounds are coded as 456-520.

Table 14: in general formula I, R$_2$=Cl, R$_3$=CH$_3$, R$_4$=R$_5$=H, R$_6$=CH$_3$, the substituent R$_1$ is consistent with those in Table 6 and corresponding to 1-65 in table 6 in turn, the representative compounds are coded as 521-585.

Table 15: in general formula I, R$_2$=Cl,

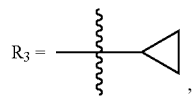

R$_4$=R$_5$=H, R$_6$CH$_3$, the substituent R$_1$ is consistent with those in Table 6 and corresponding to 1-65 in table 6 in turn, the representative compounds are coded as 586-650.

Table 16: in general formula I, R$_2$=Cl,

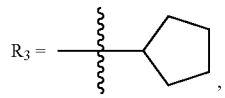

R$_4$=R$_5$=H, R$_6$=CH$_3$, the substituent R$_1$ is consistent with those in Table 6 and corresponding to 1-65 in table 6 in turn, the representative compounds are coded as 651-715.

Table 17: in general formula I, R$_2$=Cl,

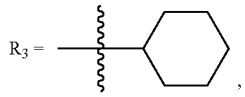

R$_4$=R$_5$=H, R$_6$=CH$_3$, the substituent R$_1$ is consistent with those in Table 6 and corresponding to 1-65 in table 6 in turn, the representative compounds are coded as 716-780.

Table 18: in general formula I, R$_2$=Cl, R$_3$=R$_4$=H, R$_5$=R$_6$=CH$_3$, the substituent R$_1$ is consistent with those, in Table 6 and corresponding to 1-65 in table 6 in turn, the representative compounds are coded as 781-845.

Table 19: in general formula I, R$_2$=Cl, R$_3$=Cl, R$_4$=H, R$_5$=R$_6$=CH$_3$, the substituent R$_1$ is consistent with those in Table 6 and corresponding to 1-65 in table 6 in turn, the representative compounds are coded as 846-910.

Table 20: in general formula I, R$_2$=Cl, R$_3$=CH$_3$, R$_4$=H, R$_5$=R$_6$=CH$_3$, the substituent R$_1$ is consistent with those in Table 6 and corresponding to 1-65 in table 6 in turn, the representative compounds are coded as 911-975.

Table 21: in general formula I, R$_2$=Cl,

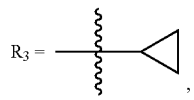

R$_4$=H, R$_5$=R$_6$=CH$_3$, the substituent R$_1$ is consistent with those in Table 6 and corresponding to 1-65 in table 6 in turn, the representative compounds are coded as 976-1040.

Table 22: in general formula I, R$_2$=Cl,

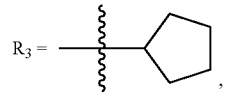

R$_4$=H, R$_5$=R$_6$=CH$_3$, the substituent R$_1$ is consistent with those in Table 6 and corresponding to 1-65 in table 6 in turn, the representative compounds are coded as 1041-1105.

Table 23: in general formula I, R$_2$=Cl,

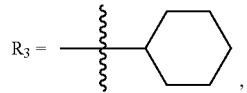

R$_4$=H, R$_5$=R$_6$=CH$_3$, the substituent R$_1$ is consistent with those in Table 6 and corresponding to 1-65 in table 6 in turn, the representative compounds are coded as 1106-1170.

In general formula I, R$_1$=CH$_3$, R$_2$=Cl, R$_3$=R$_5$=R$_6$H, the substituent R$_4$ refers to Table 24, the representative compounds are coded as 117-1310.

TABLE 24

| No. | R$_4$ |
|---|---|
| 1171 | S-i-C$_3$H$_7$ |
| 1172 | OH |
| 1173 | —C(=O)H |
| 1174 | CBr$_3$ |
| 1175 | CH$_3$ |
| 1176 | C$_2$H$_5$ |
| 1177 | n-C$_3$H$_7$ |
| 1178 | i-C$_3$H$_7$ |
| 1179 | n-C$_4$H$_9$ |
| 1180 | i-C$_4$H$_9$ |
| 1181 | t-C$_4$H$_9$ |
| 1182 | Cl$_3$ |
| 1183 | CH$_2$Br |
| 1184 | CHF$_2$ |
| 1185 | CHBr$_2$ |
| 1186 | CF$_3$ |
| 1187 | CH$_2$Cl |

TABLE 24-continued

| No. | R₄ |
|---|---|
| 1188 | CHCl₂ |
| 1189 | CCl₃ |
| 1190 | CH₂F |
| 1191 | OCH₃ |
| 1192 | OC₂H₅ |
| 1193 | OCH(CH₃)₂ |
| 1194 | OC(CH₃)₃ |
| 1195 | OCF₃ |
| 1196 | OCH₂CF₃ |
| 1197 | OCH₂F |
| 1198 | OCHF₂ |
| 1199 | SCH₃ |
| 1200 | SC₂H₅ |
| 1201 | SCH₂CH=CH₂ |
| 1202 | CH=CH₂ |
| 1203 | CH₂CH=CH₂ |
| 1204 | CH₂CH=CCl₂ |
| 1205 | C≡CH |
| 1206 | CH₂C≡CH |
| 1207 | CH₂C≡C—I |
| 1208 | CH₂OCH₃ |
| 1209 | CH₂OCH₂CH₃ |
| 1210 | CH₂CH₂OCH₃ |
| 1211 | CH₂CH₂OCH₂CH₃ |
| 1212 | CH₂OCH₂Cl |
| 1213 | CH₂OCH₂CH₂Cl |
| 1214 | CH₂CH₂OCH₂Cl |
| 1215 | CH₂SCH₃ |
| 1216 | CH₂SCH₂CH₃ |
| 1217 | CH₂CH₂SCH₃ |
| 1218 | CH₂CH₂SCH₂CH₃ |
| 1219 | CH₂SCH₂Cl |
| 1220 | CH₂SCH₂CH₂Cl |
| 1221 | CH₂CH₂SCH₂Cl |
| 1222 | SOCH₃ |
| 1223 | SOC₂H₅ |
| 1224 | SOCF₃ |
| 1225 | SOCH₂CF₃ |
| 1226 | SO₂CH₃ |
| 1227 | SO₂C₂H₅ |
| 1228 | SO₂CF₃ |
| 1229 | SO₂CH₂CF₃ |
| 1230 | SO₂NHCOCH₃ |
| 1231 | SO₂NHCH₃ |
| 1232 | SO₂N(CH₃)₃ |
| 1233 | CONHSO₂CH₃ |
| 1234 | COCH₃ |
| 1235 | COC₂H₅ |
| 1236 | CO-n-C₃H₇ |
| 1237 | CO-i-C₃H₇ |
| 1238 | CO-n-C₄H₉ |
| 1239 | CO-i-C₄H₉ |
| 1240 | CO-t-C₄H₉ |
| 1241 | COCF₃ |
| 1242 | COCH₂Cl |
| 1243 | COOCH₃ |
| 1244 | COOC₂H₅ |
| 1245 | COO-n-C₃H₇ |
| 1246 | COO-t-C₄H₉ |
| 1247 | COOCF₃ |
| 1248 | COOCH₂CH₂Cl |
| 1249 | COOCH₂CF₃ |
| 1250 | CH₂COOCH₃ |
| 1251 | CH₂COOC₂H₅ |
| 1252 | CH₂COCH₃ |
| 1253 | CH₃COC₂H₅ |
| 1254 | CONHCH₃ |
| 1255 | CONHC₂H₅ |
| 1256 | CONH-t-C₄H₉ |
| 1257 | CON(CH₃)₂ |
| 1258 | CON(C₂H₅)₂ |
| 1259 | COOCH₂CH=CH₂ |
| 1260 | COOCH₂C≡CH |
| 1261 | COOCH₂OCH₃ |
| 1262 | COOCH₂CH₂OCH₃ |
| 1263 | SNHCH₃ |
| 1264 | SNHC₂H₅ |
| 1265 | SN(CH₃)₂ |
| 1266 | SN(C₂H₅)₂ |
| 1267 | —cyclopropyl |
| 1268 | —cyclobutyl |
| 1269 | —cyclopentyl |
| 1270 | —cyclohexyl |
| 1271 | CO—O—cyclopropyl |
| 1272 | CO—O—cyclobutyl |
| 1273 | CO—O—cyclopentyl |
| 1274 | CO—O—cyclohexyl |
| 1275 | —CH₂—phenyl |
| 1276 | —CH₂—(4-Cl-phenyl) |
| 1277 | —CH₂—(2-Cl-phenyl) |
| 1278 | —CH₂—(3-Cl-phenyl) |
| 1279 | —CH₂—(4-CF₃-phenyl) |

TABLE 24-continued
| No. | R4 |
|---|---|
| 1280 | 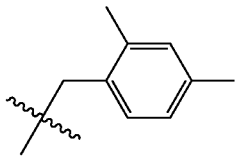 [SMILES: *Cc1ccc(C)cc1C] |
| 1281 | 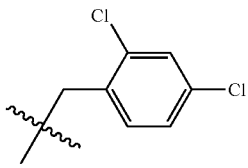 [SMILES: *Cc1ccc(Cl)cc1Cl] |
| 1282 | 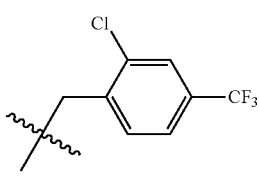 [SMILES: *Cc1ccc(C(F)(F)F)cc1Cl] |
| 1283 | 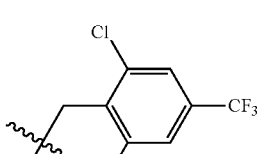 |
| 1284 | 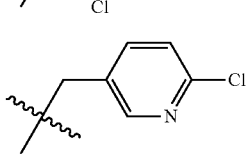 |
| 1285 | 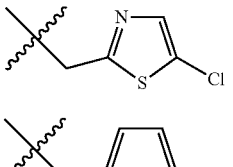 |
| 1286 | 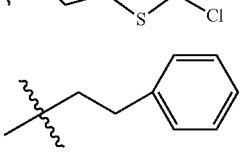 |
| 1287 | 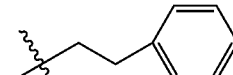 |
| 1288 |  |
| 1289 | 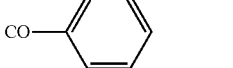 |
| 1290 | 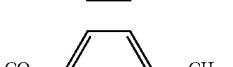 |
| 1291 | 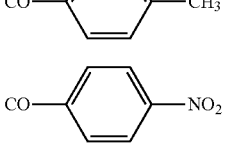 |
| 1292 | 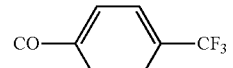 |
| 1293 | 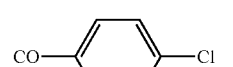 |
| 1294 |  |
| 1295 | 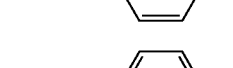 |
| 1296 | 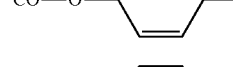 |
| 1297 | 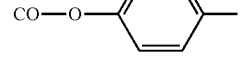 |
| 1298 | 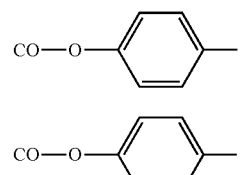 |
| 1299 |  |
| 1300 |  |
| 1301 | 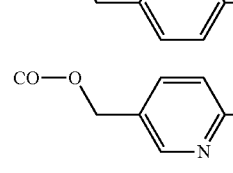 |
| 1302 | 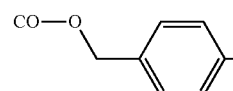 |
| 1303 |  |
| 1304 |  |
| 1305 |  |
| 1306 |  |

TABLE 24-continued

| No. | R4 |
|---|---|
| 1307 | 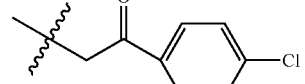 |
| 1308 | 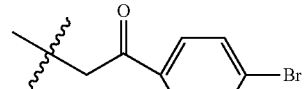 |
| 1309 | 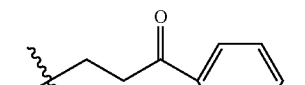 |
| 1310 | 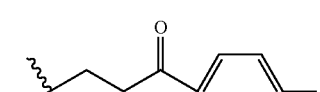 |

Table 25: in general formula I, $R_1=C_2H_5$, $R_2=Cl$, $R_3=R_5=R_6=H$, the substituent $R_4$ is consistent with those in Table 24 and corresponding to 1171-1310 in table 6 in turn, the representative compounds are coded as 1311-1450.

The salts of some compounds of the present invention are listed in Table 26, but without being restricted thereby.

TABLE 26

| No. | Structure |
|---|---|
| 1451 | 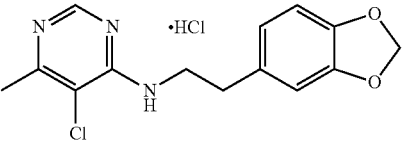 [SMILES: Cc1ncnc(NCCc2ccc3c(c2)OCO3)c1Cl ; Cl] |
| 1452 | 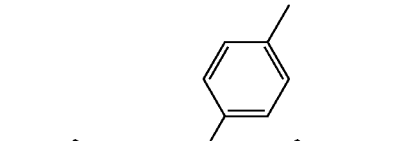 |
| 1453 | 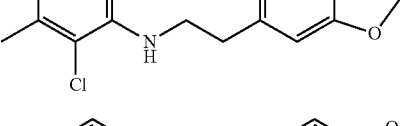 |
| 1454 | 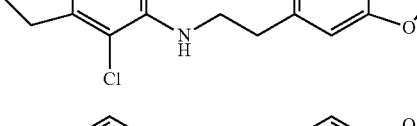 |

TABLE 26-continued

| No. | Structure |
|---|---|
| 1455 | 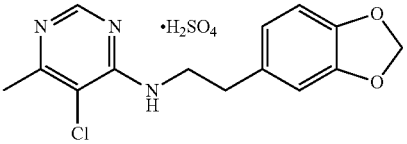 |
| 1456 | 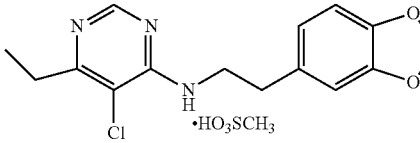 |
| 1457 | 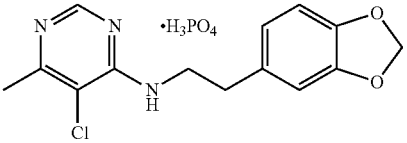 |
| 1458 | 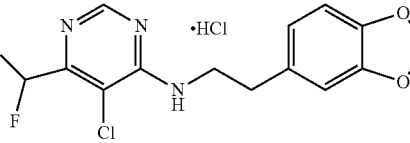 |
| 1459 | 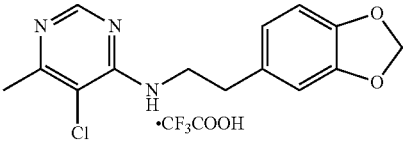 |
| 1460 | 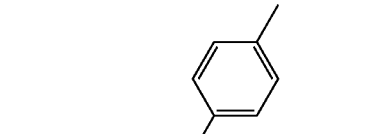 |
| 1461 | 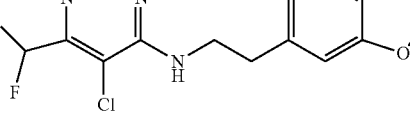 |
| 1462 | 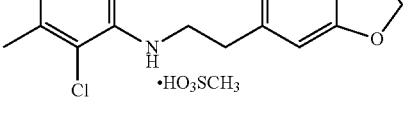 |
| 1463 | 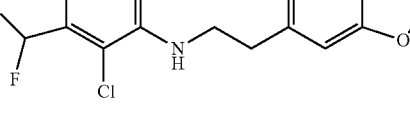 |

TABLE 26-continued

| No. | Structure |
|-----|-----------|
| 1464 | 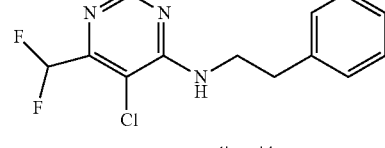 ·H₃PO₄ |
| 1465 | ·HO₃S-C₆H₄-CH₃ (p-toluenesulfonate of ethyl/Cl pyrimidine-benzodioxole amine) |
| 1466 | ·CF₃COOH |
| 1467 | ·H₂SO₄ (ethyl/Cl pyrimidine) |
| 1468 | ·HO₃SCH₃ |
| 1469 | malic acid (methyl/Cl pyrimidine) |
| 1470 | malic acid (CHF₂/Cl pyrimidine) |
| 1471 | oxalic acid (methyl/Cl pyrimidine) |

TABLE 26-continued

| No. | Structure |
|-----|-----------|
| 1472 | oxalic acid (CHF₂/Cl pyrimidine) |
| 1473 | benzoic acid (methyl/Cl pyrimidine) |
| 1474 | benzoic acid (CHF₂/Cl pyrimidine) |
| 1475 | maleic acid (methyl/Cl pyrimidine) |
| 1476 | maleic acid (CHF₂/Cl pyrimidine) |
| 1477 | citric acid (methyl/Cl pyrimidine) |
| 1478 | citric acid (CHF₂/Cl pyrimidine) |

The compounds having general formula (I) of the invention can be prepared according to the following schemes, the definitions of substituents are as defined above:

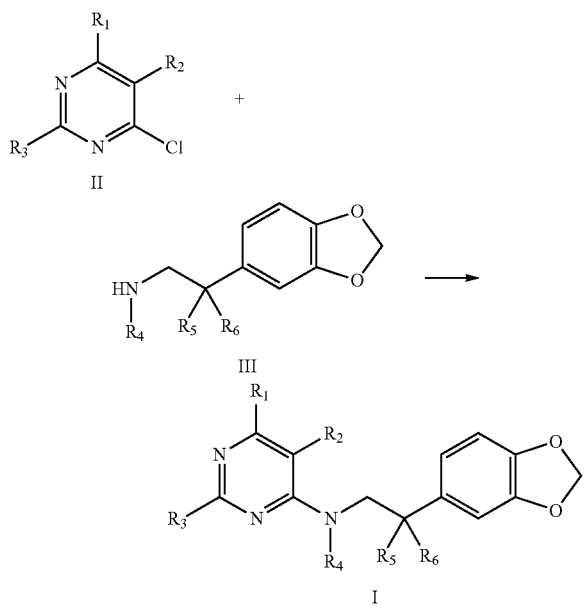

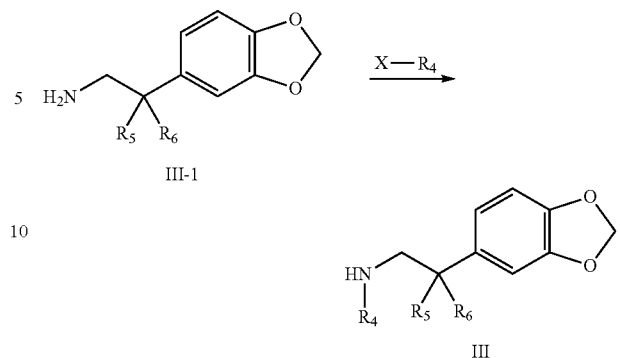

Wherein, X is halogen, methylsulfonyl or tosyl.

The preparation method of salts of the compounds having general formula I:

The preparation method of salts based on pyrimidinamine moiety:

The corresponding salts having general formula I-1 can be prepared by reaction of the compounds having general formula I with corresponding organic acids or inorganic acids, as shown in the following.

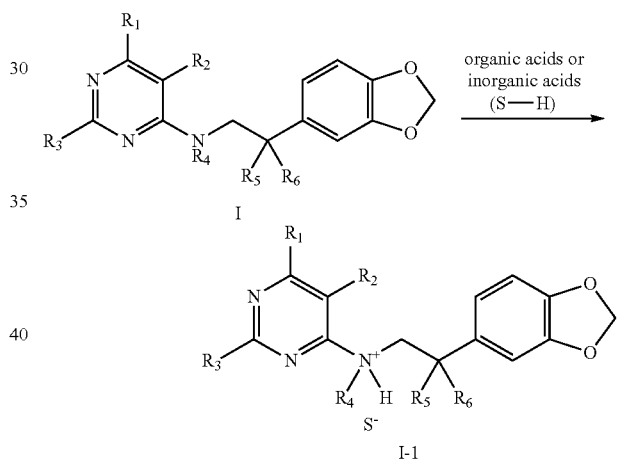

The compounds of general formula I can be obtained by reaction of intermediates II and III under basic condition.

The proper base mentioned may be selected from potassium hydroxide, sodium hydroxide, sodium carbonate, potassium carbonate, sodium bicarbonate, triethylamine, pyridine, sodium methoxide, sodium ethoxide, sodium hydride, potassium tert-butoxide or sodium tert-butoxide and so on.

The reaction was earned out in proper solvent and the proper solvent mentioned may be selected from tetrahydrofuran, 1,4-dioxane, acetonitrile, toluene, xylene, benzene, DMF, N-methyl pyrrolidone, DMSO, acetone or butanone and so on.

The proper temperature mentioned is from room temperature to boiling point of the solvent, normal temperature is from 20 to 100° C.

The reaction time is in the range of 30 minutes to 20 hours, generally being 1-10 hours.

Intermediates II can be prepared according to the method described in JP2000007662, U.S. Pat. No. 4,977,264, U.S. Pat. No. 6,090,815, US20040092402, JP09124613, U.S. Pat. No. 5,468,751, U.S. Pat. No. 4,985,426, U.S. Pat. No. 4,845,097, Recueil des Travaux Chimiques des Pays-Bas (1978), 97(11), Pages 288-92.

The preparation of intermediates III refers to the three methods shown as follows according to the different definition of $R_5$ and $R_6$.

Intermediates III, when $R_4$=$R_5$=$R_6$=H, are commercially available, or are prepared according to the method described in CN1312250A;

Intermediates III, when $R_4$=H, $R_5$ and $R_6$(≠H) defined as above, are prepared according to the method described in Farmaco, Edizione Scientifica (1965), 20(6), 456-62: JP59204177, etc.;

Intermediates III, when $R_4$≠H, are prepared from the intermediates ($R_4$=H) according to the method described in WO2004093800A:

In addition, in general formula I, the salts can also formed based on nitrogen atom of pyrimidine ring, the preparation method refers to DE19647317, JP2001504473, U.S. Pat. No. 5,925,644, WO9822446 and ZA9710187, etc.

The reaction forming salts of compounds having general formula I-1 with organic acids or inorganic acids can be carried out at room temperature to boiling point of the solvent, normal temperature is from 20 to 100° C. The reaction time is in the range of 30 minutes to 20 hours, generally being 1-10 hours. The proper solvent mentioned may be selected from water, methanol, ethanol, isopropanol, benzene, toluene, xylene, acetone, ethyl methyl ketone, methyl isobutyl ketone, chloroform, dichloromethane, methyl acetate, ethyl acetate, tetrahydrofuran, 1,4-dioxane, DMF, N-methyl pyrrolidone or DMSO and so on.

The acids, which can be used to form salts with compounds having general formula I-1, includes hydrochloric acid, sulphuric acid, phosphorous acid, formic acid, acetic acid, trifluoroacetic acid, oxalic acid, methanesulfonic acid, p-toluenesulfonic acid, benzoic acid, phthalic acid, maleic acid, sorbic acid, malic acid or citric acid, etc. The further preferred acids are hydrochloric acid, sulphuric acid, phosphorous acid, trifluoroacetic acid, methanesulfonic acid or p-toluenesulfonic acid.

Although the compounds having general formula I and some compounds reported in prior art are both belong to substituted pyrimidines, there are still some obvious differences in structure between them. It is due to these differences in structure that lead to compounds of present invention with better fungicidal and/or insecticidal/acaricidal and antitumor activities.

The compounds of general formula I show excellent activity against both many plant pathogens/diseases in agricultural and other fields, and insects/mites, at the same time, they also have some antitumor activity. Therefore the technical scheme of the present invention also includes the uses of the compounds having general formula I or their salts to prepare fungicides, insecticides/acaricides in agricultural and other fields and to prepare antitumor agents in pharmaceutical fields.

The present invention is explained by the following examples of plant disease, but without being restricted thereby.

The compounds of general formula I can be used to control these plant diseases: Oomycete diseases, such as downy mildew (cucumber downy mildew, rape downy mildew, soybean downy mildew, downy mildew of beet, downy mildew of sugarcane, tobacco downy mildew, pea downy mildew, vegetable sponge downy mildew, chinese wax gourd downy mildew, muskmelon downy mildew, chinese cabbage downy mildew, spinach downy mildew, radish downy mildew, grape downy mildew, onion downy mildew), white rust (rape white rust, chinese cabbage white rust), damping-off disease (rape damping-off, tobacco damping-off, tomato damping-off, pepper damping-off, eggplant damping-off, cucumber damping-off, cotton damping-off), pythium rot (pepper soft stale disease, vegetable sponge cottony leak, chinese wax gourd cottony leak), blight (broad bean phytophthora blight, cucumber phytophthora blight, pumpkin phytophthora rot, chinese wax gourd phytophthora blight, watermelon phytophthora blight, muskmelon phytophthora blight, pepper phytophthora blight, chinese chives phytophthora blight, carlic phytophthora blight, cotton phytophthora blight), late blight (potato late blight, tomato late blight) and so on; diseases caused by Deuteromycotina, such as wilt disease (sweet potato fusarium wilt, cotton fusarium wilt disease, sesame wilt disease, fusarium wilt disease of costarbean, tomato fusarium wilt, bean fusarium wilt, cucumber fusarium wilt, vegetable sponge fusarium wilt, pumpkin fusarium wilt, chinese wax gourd fusarium wilt, watermelon fusarium wilt, muskmelon fusarium wilt, pepper fusarium wilt, broad bean fusarium wilt, fusarium wilt disease of rape, fusarium wilt disease of soybean), root rot (pepper root rot, eggplant root rot, bean fusarium root-rot, cucumber fusarium root rot, balsam pear fusarium root rot, cotton black root rot, broad bean thielaviopsis root rot), drooping disease (cotton soreshin, sesame soreshin, pepper rhizoctonia rot, cucumber rhizoctonia rot, chinese cabbage rhizoctonia rot), anthracnose (sorghum anthracnose, cotton anthracnose, kenaf anthracnose, jute anthracnose, flax anthracnose, tobacco anthracnose, mulberry anthracnose, pepper anthracnose, eggplant anthracnose, bean anthracnose, cucumber anthracnose, balsam pear anthracnose, summer squash anthracnose, chinese wax gourd anthracnose, watermelon anthracnose, muskmelon anthracnose, litchi anthracnose), verticillium wilt (cotton verticiliium wilt, verticillium wilt of sunflower, tomato verticillium wilt, pepper verticillium wilt, eggplant verticillium wilt), scab (summer squash scab, chinese wax gourd scab, muskmelon scab), gray mold (cotton boll gray mold, kenaf gray mold, tomato gray mold, pepper gray mold, bean gray mold, celery gray mold, spinach gray mold, kiwi fruit gray mold rot), brown spot (cotton brown spot, jute brown spot, beet sercospora leaf spot, peanut brown spot, pepper brown leaf spot, chinese wax gourd corynespora leaf spot, soybean brown spot, sunflower brown spot, pea ascochyta blight, broad bean brown spot), black spot (flax black spot, rape alternaria leaf spot, sesame black spot, sunflower alternaria leaf spot, costarbean alternaria leaf spot, tomato nail head spot, pepper black fruit spot, eggplant black spot, bean leaf spot, cucumber alternaria blight, celery alternaria black leaf spot, carrot alternaria black rot, carrot leaf blight, apple alternaria rot, peanut brown spot), spot blight (tomato septoria leaf spot, pepper septoria leaf spot, celery late blight), early blight (tomato early blight, pepper early blight, eggplant early blight, potato early blight, celery early blight), ring spot (soybean zonate spot, sesame ring spot, bean zonate spot), leaf blight (sesame leaf blight, sunflower leaf blight, watermelon alternaria blight, muskmelon alternaria spot), basal stem rot (tomato basal stem rot, bean rhizoctonia rot), and others (corn northern leaf spot, kenaf damping-off, rice blast, millet black sheath, sugarcane eye spot, cotton aspergillus boll rot, peanut crown rot, soybean stem blight, soybean black spot, muskmelon alternaria leaf blight, peanut web blotch, tea red leaf spot, pepper phyllosticta blight, chinese wax gourd phyllosticta leaf spot, celery black rot, spinach heart rot, kenaf leaf mold, kenaf brown leaf spot, Jute stem blight, soybean cercospora spot, sesame leaf spot, costarbean gray leaf spot, tea brown leaf spot, eggplant cercospora leaf spot, bean cercospora leaf spot, balsam pear cercospora leaf spot, watermelon cercospora leaf spot, jute dry rot, sunflower root and stem rot, bean charcoal rot, soybean target spot, eggplant corynespora leaf spot, cucumber corynespora target leaf spot, tomato leaf mold, eggplant fulvia leaf mold, broad bean chocolate spot) and so on; diseases caused by Basidiomycete, such as rust (wheat stripe rust, wheat stem rust, wheat leaf rust peanut rust, sunflower rust, sugarcane rust, chinese chives rust, onion rust, millet rust, soybean rust), smut (corn head smut, corn smut, sorghum silk smut, sorghum loose kernel smut, sorghum hard smut, sorghum smut, millet kernel smut, sugarcane smut, bean rust), and others (for example, wheat sheath blight and rice sheath blight) and so on; diseases caused by Ascomycete, such as powdery mildew (wheat powdery mildew, rape powdery mildew, powdery mildew of sesame, powdery mildew of sunflower, beet powdery mildew, eggplant powdery mildew, pea powdery mildew, vegetable sponge powderery mildew, pumpkin powdery mildew, summer squash powdery mildew, chinese wax gourd, muskmelon powdery mildew, grape powdery mildew, broad bean powdery mildew), sclerotinia rot (flax sclertiniose, rape sclertiniose, soybean sclertiniose, peanut sclertiniose, tobacco sclerotinia rot, pepper sclerotinia rot, eggplant sclerotinia rot, bean sclerotinia rot, pea sclerotinia rot, cucumber sclerotinia rot, balsam pear sclerotinia rot, chinese wax gourd sclerotinia rot, watermelon sclerotinia disease, celery stem rot), scab (apple scab, pear scab) and so on. Especially, the compounds of the present invention exhibit very good control against corn southern rust, rice blast, cucumber gray mold and cucumber downy mildew at very low doses.

The compounds of general formula I can be used to control these insects: Coleoptera, such as *Acanthoscelides* spp., *Acanthoscelides obtectus, Agrilus planipennis, Agriotes* spp., *Anoplophora glabripennis, Anthonomus* spp., *Anthonomus grandis, Aphidius* spp., *Apion* spp., *Apogonia* spp., *Atacnius spretulus, Atomaria linearis*, pygmy mangold beetle, *Aulacophore* spp., *Bothynoderes punctiventris, Bruchus* spp., *Bruchus pisorum, Cacoesia, Cacoesia* spp., *Caliosobruchus maculatus, Carpophilus hemipteras, Cassida vittata, Cerosterna* spp., *Cerotonia, Cerotoma* spp., *Cerotoma trifur cata, Ceutorhynchus* spp., *Ceutorhynchus assimilis*, cabbage seedpod weevil, *Ceutorhynchus napi*, cabbage *curculio, Chaetocnema* spp., *Colaspis* spp., *Conoderus scalaris, Conoderus stigmosus, Conotrachelus nenuphar, Cotinus nitidis*, Green June beetle, *Crioceris asparagi, Cryptolestes ferruginous*, rusty grainbeetle, *Cryptolestes pusillus, Cryptolestes turcicus* Turkish grain beetle, *Ctenicera* spp., *Curculio* spp., *Cyclocephala* spp., *Cylindrocpturus adspersus*, sunflower stem weevil, *Deporaus marginatus*, mango leaf-cutting weevil, *Dermestes lardarius, Dermestes maculates, Diabrotica* spp., *Epilachna varivestis, raustinus cubae, Hylobius pales*, pales weevil, *Hypera* spp., *Hypera postica, Hyperdoes* spp., Hyperodes weevil, *Hypothenemus hampei, Ips* spp., engravers, *Lasioderma serricorne, Leptinotarsa decemlineata, Liogenys fuscus, Liogenys suturalis, Lissorhoptrus oryzophilus, Lyctus* spp., powder post beetles, *Maecolaspis joliveti, Megascelis* spp., *Melanotus communis, Meligethes* spp., *Meligethes aeneus*, blossom beetle, *Melolontha melolontha, Oberea brevis, Oberea linearis, Oryctes rhinoceros*, date palm beetle, *Oryzaephilus mercator*, merchant grain beetle, *Oryzaephilus surinamensis*, sawtoothed grain beetle, *Otiorhynchus* spp., *Oulema melanopus*, cereal leafbeetle, *Oulema oryzae, Pantomorus* spp., *Phyliophaga* spp., *Phvliophaga cuyabana, Phyllotreta* spp., *Phynchites* spp., *Popillia japonica, Prostephanus truncates*, larger grain borer, *Rhizopertha dominica*, lesser grain borer, *Rhizolrogus* spp., Europoean chafer, *Rhynehophorus* spp., *Scolytus* spp., *Shenophorus* spp. *Sitona lincatus*, pea leaf weevil, *Sitophilus* spp., *Sitophilus granaries*, granary weevil, *Sitophilus oryzae*, rice weevil, *Stegobium paniceum*, drugstore beetle, *Tribolium* spp., *Tribolium castaneum*, (red flour beetle, *Tribolium confusum*, confused flour beetle, *Trogoderma variabile*, warehouse beetle and *Zabrus tenebioides*.

Dermaptera.

Dictyoptera, such as *Blattella germanica*, German cockroach, *Blatta orientalis, Parcoblatta pennylvanica, Periplaneta americana*, American cockroach, *Periplaneta australoasiae*, Australian cockroach, *Periplaneta brunnca*, brown cockroach, *Periplaneta fuliginosa*, smokybrown cockroach, *Pyncoselus suninimensis*, Surinam cockroach and *Supella longipalpa*, brownbanded cockroach)).

Diptera, such as *Aedes* spp., *Agromyza frontella*, alfalfa blotch leafminer, *Agromyza* spp., *Anastrepha* spp., *Anastrepha suspensa*, Caribbean fruit fly, *Anopheles* spp., *Batrocera* spp., *Bactrocera cucurbitae, Bactrocera dorsalis, Ceratitis* spp., *Ceratitis capitata, Chrysops* spp., *Cochliomyia* spp., *Contarinia* spp., *Culex* spp., *Dasineura* spp., *Dasineura brassicae, Delia* spp.), *Delia platura*, seedcorn maggot), *Drosophila* spp., *Fannia* spp., *Fannia canicularis*, little house fly, *Fannia scalaris, Gasterophilus intestinalis, Gracillia perseae, Haematobia irritans, Hylemyia* spp., root maggot, *Hypoderma lineatum*, common cattle grab, *Liriomyza* spp., *Liriomyza brassica*, serpentine leafminer, *Melophagus ovinus, Musca* spp., muscid fly, *Musca autumnalis*, face fly, *Vusca domestica*, house fly, *Oestrus ovis*, sheep bot fly, *Oscinella frit, Pegomyia betae*, (beet leafminer, *Phorbia* spp., *Psila rosae*, carrotrust fly, *Rhagoletis cerasi*, cherry fruit fly, *Rhagoletis pomonella*, apple maggot, *Sitodiplosis mosellana*, orange wheat blossom midge, *stomoxys calcitruns*, stable fly, *Tahanus* spp. and *Tipula* spp.

Hemiptera, such as *Acrosternum hilare*, green stink bug, *Blissus leucopterus*, chinch bug, *Calocoris norvegicus*, potato mirid, *Cimex hemipterus*, tropical bed bug, *Cimex lectularius*, bed bug, *Daghertus fasciatus, Dichelops furcatus, Dysdercus suturellus*, cotton stainer, *Edessa meditabunda, Eurygaster maura*, cereal bug, *Euschistus heros, Euschistus servus*, brown stink bug, *Helopeltis antonii, Helopeltis theivora*, tea blight plantbug, *Lagynotomus* spp., *Leptocorisa oratorius, Leptocorisa varicomi, Lygus* spp., plant bug, *Lygus hesperus*, western tarnished plant bug, *Maconellicoccus hirsutus, Neurocolpus longirostris, Nezara viridula*, southern green stink bug, *PhyLocoris* spp., *Phytocoris californicus, Phytocoris relativus, Piezodorus guildingi, Poecilocapsus lineatus*, fourlined plant bug, *Psallus vaccinicola, Pseudacysta perseae, Scaptocoris castanea* and *Triatoma* spp., bloodsuckingeonenose bug, kissing bug)).

Homoptera, such as *Acrythosiphonpisum*, pea aphid, *Adelges* spp., adelgids, *Aleurodes proletella, Aleurodicus disperses, Aleurothrixus flecosus*, woolly whitefly, *Aluacaspis* spp., *Amrasca bigutella bigutella, Aphropbora* spp., leafhopper, *Aonidiella aurantii*, California red scale, *Aphis* spp., *Aphis gossypii*, cotton aphid, *Aphis pomi*, apple aphid, *Aulacorthitm solan*, foxglove aphid, *Bemisia* spp., *Bemisia argentifolii, Bemisia tabaci*, sweetpotato whitefly, *Brachycolus noxius*, Russian aphid, *Brachycorynelia asparagi*, asparagus aphid, *Brevennia rehi, Brevicoryne brassicae, Ceroplastes* spp., *Ceroplastes rubens*, red wax scale, *Chionaspis* spp., *Chrysomphalus* spp., *Coccus* spp., *Dysaphis plantaginea*, rosy apple aphid, *Empoasca* spp., *Eriosoma lanigerum*, woolly apple aphid, *Icerya purchasi*, cottony cushion scale, *Idioscopus nitidulus*, mango leafhopper, *Laodelphax striaiellus*, smaller brown planthopper, *Lepidosaphes* spp., *Macrosiphum* spp., *Macrosiphum euphorbiae*, potato aphid, *Macrosiphum granarium*, (English grain aphid, *Macrosiphum rosae*, rose aphid, *Macrosteles quadrilineatus*, aster leafhopper, *Mahanarva frimbiolata, Metopolophium dirhodum*, rose grain aphid, *Midis longicornis, Myzus persicae*, green peach aphid, *Nephotettix* spp., *Nephotettix cinctipes*, green leafhopper, *Nilaparvata lugens*, brown planthopper, *Parlatoria pergandii*, chaff scale, *Parlatoria ziziphi*, ebony scale, *Peregrinus maidis*, corn delphacid, *Philaenus* spp., *Phylloxera vitifoliae*, grape phylloxera, *Physokermes piceae*, spruce bud scale, *Planococcus* spp., *Pseudococcus* spp., *Pseudococcus brevipes*, pine apple mealybug, *Quadraspidiotus pemiciosus*, San Jose scale, *Rhapalosiphum* spp., *Rhapalosiphum maida*, corn leaf aphid, *Rhapalosiphum padi*, oatbird-cherry aphid, *Saissetia* spp., *Saissetia oleae, Schizaphis graminum*, greenbug, *Sitobion avenge, Sogatella furcifera*, white-backed planthopper, *Therioaphis* spp., *Toumeyella* spp., *Toxoptera* spp., *Trialeurodes* spp., *Trialeurodes vaporariorum*, greenhouse whitefly, *Trialeurodes abutiloneus*, bandedwing whitefly, *Unaspis* spp., *Unaspis yanonensis*, arrowhead scale and *Zulia entreriana*.

Hymenoptera, such as *Acromyrrmex* spp., *Athalia rosae, Atta* spp., leafcutting ants, *Camponotus* spp., carpenter ant, *Diprion* spp., sawfly, *Formica* spp., *Iridomyrmex humilis*, Argentineant, *Monomorium* ssp., *Monomorium minumum*, little black ant, *Monomorium pharaonis*, haraoh ant, *Neodiprion* spp., *Pogonomyrmex* spp., *Polistes* spp., paper wasp, *Solenopsis* spp., *Tapoinoma sessile*, odorous house ant, *Tetranomorium* spp., pavement ant, *Vespula* spp., yellow jacket and *Xylocopa* spp., carpenter bee.

Isoptera, such as *Coptotermes* spp., *Coptotermes curvignathus, Coptotermes frenchii), Coptotermes formosanus*, Formosan subterranean termite, *Cornitermes* spp., nasute termite, *Cryptotermes* spp., *Heterotermes* spp., desert subterranean termite, *Heterotermes aureus*, *Kalotermes* spp., *Incistitermes* spp., *Macrotermes* spp., fungus growing termite, *Marginitermes* spp., *Microcerotermes* spp., harvester termite, *Microtermes obesi*, *Procornitermes* spp., *Reticulitermes* spp., *Reticulitermes banyulensis*, *Reticulitermes grassei*, *Reticulitermes flavipes*, *Reticulitermes hageni*, *Reticulitermes hesperus*, *Reticulitermes santonensis*, *Reticulitermes speratus*, *Reticulitermes tibialis*, *Reticulitermes virginicus*, *Schedorhinotermes* spp. and *Zootermopsis* spp.

Lepidoptera, such as *Achoea janata*, *Adoxophyes* spp., *Adoxophyes orana*, *Agrotis* spp., *Agrotis ipsilon*, *Alabama argillacea*, cotton leafworm, *Amorbia cuneana*, *Amyelosis transitella*, navel orangeworm, *Anacamptodes defectaria*, *Anarsia lineatella*, peach twig borer, *Anomis sabulijera*, jute looper, *Anticarsia gemmatalis*, velvetbean caterpillar, *Archips argyrospila*) (fruit tree leafroller, *Archips rosana*, rose leaf roller, *Ar gyrotaenia* spp., tortricid moths, *Argyrotaenia citrana*, orange tortrix, *Autographa gamma*, *Bonagota cranaodes*, *Borbo cinnara*, rice leaf folder, *Bucculatrix thurberiella*, cotton leafperforator, *Caloptilia* spp., *Capua reticulana*, *Carposina niponensis*, peach fruit moth, *Chilo* spp., *Chlumetia transversa*, mango shoot borer, *Choristoneura rosaceana*, oblique banded leaf roller, *Chrysodeixis* spp., *Cnaphalocerus medinalis*, grass leafroller, *Colias* spp., *Conpomorpha cramerella*, *Cossus cossus*, *Crambus* spp., Sod webworms, *Cydia funebrana*, plum fruit moth, *Cydia molesta*, oriental fruit moth, *Cydia nignicana*, pea moth, *Cydia pomonella*, codling moth, *Darna diducta*, *Diaphania* spp., stem borer, *Diatr aea* spp., stalk borer, *Diatraea saccharalis*, sugarcane borer, *Diatraea graniosella*, southwester corn borer, *Earias* spp., *Earias insulata*, Egyptian bollworm, *Earias vitella*, rough northern bollworm, *Ecdytopopha aurantianum*, *Elasmopalpus lignosellus*, lesser cornstalk borer, *Eprphysias postruttana*, light brown, apple moth, *Ephestia* spp., *Ephestia cautella*, almond moth, *Ephestia elutella*, tobbaco moth, *Ephestia kuehniella*, Mediterranean flour moth, *Epimeces* spp, *Epinotia aporema*, *Erionota thrax*, banana skipper, *Eupoecilia ambiguella*, grape berry moth, *Euxoa auxiliaris*, army cutworm, *Feltia* spp., *Gortyna* spp., *Grapholita molesta*, oriental fruit moth, *Hedylepta indicata*, bean leaf webber, *Helicoverpa* spp., *Helicoverpa armigera*, cotton bollworm, *Helicoverpa zea*, *Heliothis* spp., *Heliothis virescens*, tobacco budworm, *Hellula undalis*, cabbage webworm, *Indarbela* spp. *Keiferia lycopersicella*, tomato pinworm, *Leucinodes orbonalis*, eggplant fruit borer, *Leucoptera malifoliella*, *Lithocollectis* spp., *Lobesia botrana*, grape fruit moth, *Loxagrotis* spp., *Loxagrotis albicosta*, western bean cutworm, *Lymantria dispar*, gypsy moth, *Lyonetiaclerkella*, apple leafminer, *Mahasena corbetti*, oil palm bagworm, *Malacosoma* spp., tent caterpillars, *Mamestra brassicae*, cabbage armyworm, *Maruca testulalis*, *Metisa plana*, *Mythimna unipuncta*, true armyworm, *Neoleucinodes elegantalis*, small tomato borer, *Nymphula depunctalis*, rice caseworm, *Operophthera brumata*, winter moth, *Ostrinia nubilalis*, European corn borer, *Oxydia vesulia*, *Pandemis cerasana*, common currant tortrix, *Pandemis heparana*, brown apple tortrix, *Papilio demodocus*, *Pectinophora gossypiella*, pink bollworm, *Peridroma* spp., *Peridroma saucia*, variegated cutworm, *Perileucoptera coffeelia*, white coffee leafminer, *Phthorimaea operculella*, potato tuber moth, *Phylloenisitis citrella*, *Phyllonorycter* spp., *Pieris rapae*, imported cabbageworm, *Plathypena scabra*, *Plodia interpunctella*, Indian meal moth, *Plutelia xylostella*, diamondback moth, *Polychrosis viteana*, grape berry moth, *Prays endocarps*, *Prsys oleae*, olive moth, *Pseudaletia* spp., *Pseudaletia unipunctata*, *Pseudoplusia includens*, soybean looper, *Rachiplusia nu*, *Scirpophaga incertulas*, *Sesamia* spp., *Sesamia inferens*, pink rice stemborer, *Sesamia nonagrioides*, *Setora nitens*, *Sitotroga cerealella*, Angoumois grain moth, *Sparganothis pilleriana*, *Spodoptera* spp., *Spodoptera exigua*, beet armyworm, *Spodoptera fugiperda*, fall armyworm, *Spodoptera oridania*, southern armyworm, *Synanthedon* spp., *Thecla basilides*, *Thermisia gemmatalis*, *Tineola bisselliella*, webbing clothes moth, *Trichoplusia ni*, cabbage looper, *Tuts absoluta*, *Yponomeuta* spp., *Zeuzeracoffeae*, red branch borer and *Zeuzera pyrina*, eopard moth.

Mallophaga, chewing lice, such as *Bovicola ovis*, sheep biting louse, *Menacanthus stramineus*, chicken body louse and *Menopon gallinea*, common hen house, Orthoptera, such as *Anabrus simplex*, Mormon cricket, Gtyllotalpidae, mole cricket, *Locusta migratoria*, *Melanoplus* spp., *Microcentrum retinerve*, angular winged katydid, *Pterophylla* spp., *histocerca gregaria*, *Scudderia furcata*, fork tailed bush katydid and *Valanga nigricorni*.

sucking louse, such as *Haematopinus* spp., *Linognathus ovillus*, sheep louse, *Pediculus humanus capitis*, *Pediculus humanus humanus* and *Pthirus pubis*, crab louse.

Siphonaptera, such as *Ctenocephal ides canis*, dog flea, *Ctenocephalides felis*, cat flea and *Pulex irritans*) (human flea).

Thysanoptera, such as *Frankliniella fusca*, tobacco thrip, *Frankliniella occidentalis*, western flower thrips, *Frankliniella shultzei*, *Frankliniella williamsi*, corn thrip, *Heliothrips haemorrhaidalis*) (greenhouse thrip), *Riphiphorothrips cruentatus*, *Scirtothrips* spp, *Scirtothrips cirri*, citrus thrip, *Scirtothrips dorsalis*, yellow tea thrips, *Taeniothrips rhopalantennalis* and *Thrips* spp.).

Thysanura, bristletail, such as *Lepisma* spp, silverfish and *Thermobia* spp.

Acarina, mite and tick, such as *Acarapsis woodi*, tracheal mite of honeybee, *Acarus* spp., *Acarus siro*, grain mite, *Aceria mangiferae*, mango bud mite, *Aculops* spp., *Aculops lycopersici*, tomato russet mite, *Aculops pelekasi*, *Aculus pelekassi*, *Aculus schlechtendali*, apple rust mite, *Amblyomma americanum*, lone star tick, *Boophilus* spp., *Brevipalpus obovatus*, privet mite, *Brevipalpus phoenicis*, red and black flat mite, *Demodex* spp., mange mites, *Dermacentor* spp., *Dermacentor variabilis*, american dog tick, *Dermatophagoides pteronyssinus*, house dust mite, *Eotetranycus* spp., *Eotetranychus carpini*, yellow spider mite, *Epitimeras* spp., *Eriophyes* spp., *Iodes* spp., *Metatetranycus* spp., *Notoedres cati*, *Oligonychus* spp., *Oligonychus coffee*, *Oligonychus ilicus*, southernred mite, *anonychus* spp., *Panonychus cirri*, citrus red mite, *Panonychus ulmi*, European red mite, *Phyllocoptruta oleivora*, citrus rust mite, *Polyphagotarsonemun latus*, broad mite, *Rhipicephalus sanguineus*, brown dog tick, *Rhizoglyphus* spp., bulb mite, *Sarcoptes scabiei*, itch mite, *Tegolophus perseaflorae*, *Tetranychus* spp., *Tetranychus urticae*, twospotted spider mite and Varroa destructor.

Nematoda, such as *Aphelenchoides* spp., bud and leaf & pine wood nematode, *Belonolaimus* spp., sting nematodes, *Criconemelia* spp., ring nematodes, *Dirofilaria immitis*, dog heartworm, *Ditylenchus* spp., *Heterodera* spp., cyst nematode, *Heterodera zeae*, corn cyst nematode, *Hirschmanniella* spp., root nematodes, *Hoplolaimus* spp., lance nematodes, *Meloidogyne* spp., (*Meloidogyne incognita*, *Onchocerca volvulus*, hook-tail worm, *PraLylenchus* spp., lesion nematode, *Radopholus* spp., burrowing nematode and *Rotylenchus reniformis*) (kidney-shaped nematode.

Symphyla, such as *Scutigerella immaculata*.

Especially, the compound of the present invention provides excellent control effects against peach aphid, diamondback moth, armyworm, and carmine spider mite at lower dosage.

Thanks to their positive characteristics, the compounds mentioned above can be advantageously used in protecting crops of farming and gardening, domestic and breeding animals, as well as environments frequented by human beings, from pathogens, insects and pest mites.

In order to obtain desired effect, the dosage of the compound to be applied can vary with various factors, for example, the used compound, the protected crop, the type of harmful organism, the degree of infestation, the climatic conditions, the application method and the adopted formulation.

The dosage of compounds in the range of 10 g to 5 kg per hectare can provide a sufficient control.

A further object of the present invention also includes fungicidal, insecticidal/acaricidal compositions containing the compounds having general formula I as active ingredient, and the weight percentage of the active ingredient in the composition is 1-99%. The fungicidal, insecticidal/acaricidal compositions also include the carrier being acceptable in agriculture, forestry, public health.

The compositions of the present invention can be used in the form of various formulations. Usually, the compounds having general formula I as active ingredient can be dissolved in or dispersed in carriers or made to a formulation so that they can be easily dispersed as an fungicide or insecticide. For example: these chemical formulations can be made into wettable powder, oil miscible flowable, aqueous suspension, aqueous emulsion, aqueous solution or emulsifiable concentrates. Therefore, in these compositions, at least a liquid or solid carrier is added, and usually suitable surfactant(s) can be added when needed.

Still also provided by the present invention are the application methods for controlling phytopathogenic fungi, insects, pest mites: which is to apply the compositions of the present invention to the phytopathogenic fungi, insects, pest mites as mentioned above or their growing loci. The suitable effective dosage of the compounds of the present invention is usually within a range of 10 g/ha to 1000 g/ha, preferably from 20 g/ha to 500 g/ha. For some applications, one or more other fungicides, insecticides/acaricides, herbicides, plant growth regulators or fertilizer can be added into the fungicidal, insecticidal/acaricidal compositions of the present invention to make additional merits and effects.

Besides application fields mentioned above, the compounds having general formula I of the present invention can also be used to prepare anticancer drugs to cure or relieve cancer in some tissue or organ. The cancer mentioned includes, but without being restricted thereby, colon cancer, liver cancer, lymphomas, lung cancer, esophageal cancer, breast cancer, central nervous system tumors (CNST), melanoma, ovarian cancer, cervical cancer, kidney cancer, leukaemia, prostate cancer, pancreatic cancer, bladder cancer, rectal cancer or stomach cancer. Particularly, the compounds having general formula I of the present invention have better growth inhibition effect on bladder cancer cells.

It should be noted that variations and changes are permitted within the claimed scopes in the present invention.

DETAILED DESCRIPTION OF THE INVENTION

The present invention is illustrated by the following examples, but without being restricted thereby. (All raw materials are commercially available unless otherwise specified.)

PREPARATION EXAMPLES

Example 1

The Preparation of Intermediate 4,5-dichloro-6-methylpyrimidine

1) The Preparation of 4-hydroxyl-5-chloro-6-methylpyrimidine

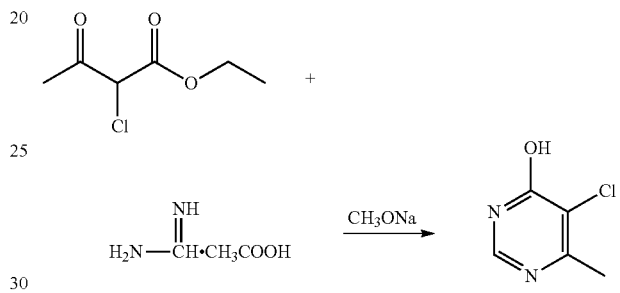

8.80 g (0.16 mol) of CH$_3$ONa in methanol was added slowly to a solution of 11.30 g (0.11 mol) of formimidamide in 50 mL of methanol at room temperature under stirring, the mixture was stirred for another 2 h after addition at room temperature. Followed by addition of 11.17 g (0.068 mol) of ethyl 2-chloro-3-oxobutanoate, the mixture was continued stirring for another 5-7 h at room temperature. After the reaction was over by Thin-Layer Chromatography monitoring, the reaction mixture was concentrated under reduced pressure and pH was adjusted to 5-6 with HCl, and then filtered to afford orange-yellow solid, the water phase was extracted with ethyl acetate (3×50 ml), dried over anhydrous magnesium sulfate, filtered and then concentrated under reduced pressure. The residue was dissolved to 50 ml of ethyl acetate, stand overnight to obtain 6.48 g as orange-yellow solid with yield of 66%, m.p, 181~184° C.

2) The Preparation of Intermediate 4,5-dichloro-6-methylpyrimidine

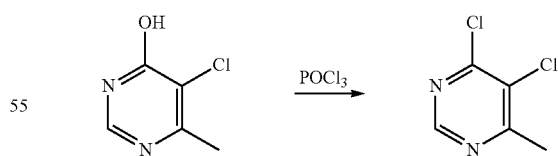

50 ml of POCl$_3$ was added dropwise to a solution of 14.5 g (0.1 mol) of 4-hydroxyl-5-chloro-6-methylpyrimidine in 50 mL of toluene, the mixture was refluxed for 5-7 h after addition. After the reaction was over by Thin-Layer Chromatography monitoring, the reaction mixture was concentrated under reduced pressure to remove toluene and extra POCl$_3$, and then poured into ice water. The water phase was extracted with ethyl acetate (3×50 ml), the organic phases were emerged, dried over anhydrous magnesium sulfate, filtered and then concentrated under reduced pressure. The residue was purified through silica column to give 14.43 g as yellow liquid with yield of 88.5%.

Example 2

The Preparation of Intermediate 4,5-dichloro-6-(difluoromethyl)pyrimidine

1) The Preparation of 4-hydroxyl-5-chloro-6-(difluoromethyl)pyrimidine

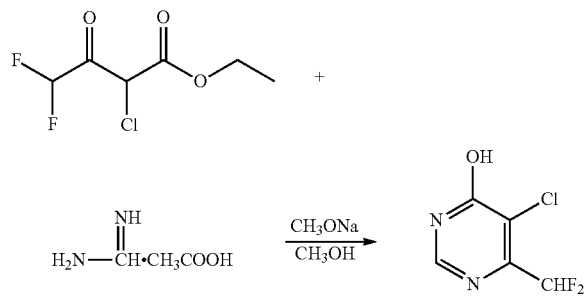

A solution of 71.9 g (0.70 mol) of formimidamide in 150 mL of methanol was stirred at 5-10° C., 64.6 g (1.20 mol) of CH₃ONa in methanol prepared and cooled to room temperature ahead of time was added slowly to the above solution under stirring, followed by addition of 100 g (0.50 mol) of ethyl 2-chloro-4,4-difluoro-3-oxobutanoate in 100 ml of methanol, the mixture was continued stirring for another 3-4 h at room temperature. After the reaction was over by Thin-Layer Chromatography monitoring, the reaction mixture was concentrated under reduced pressure and pH was adjusted to 5-6 with HCl, and then filtered to afford 65 g as white solid with yield of 73%. m.p. 204~206° C.

2) The Preparation of 4,5-dichloro-6-(difluoromethyl)pyrimidine

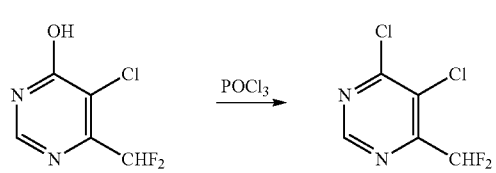 [SMILES: Oc1ncnc(C(F)F)c1Cl ; "POCl3" ; FC(F)c1ncnc(Cl)c1Cl]

100 ml of POCl₃ was added dropwise to a solution of 65.0 g (0.36 mol) of 4-hydroxyl-5-chloro-6-(difluoromethyl)pyrimidin in 150 mL of toluene, the mixture was refluxed for 3-5 h after addition. After the reaction was over by Thin-Layer Chromatography monitoring, the reaction mixture was concentrated under reduced pressure to remove toluene and extra POCl₃, and then poured into ice water. The water phase was extracted with ethyl acetate (3×50 ml), the organic phases were emerged, washed with saturated sodium bicarbonate, dried over anhydrous magnesium sulfate, filtered and then concentrated under reduced pressure. The residue was purified through silica column to give 64.5 g as yellow liquid, cooled to be solid in refrigerator with yield of 90%.

Example 3

The Preparation of Compound 5

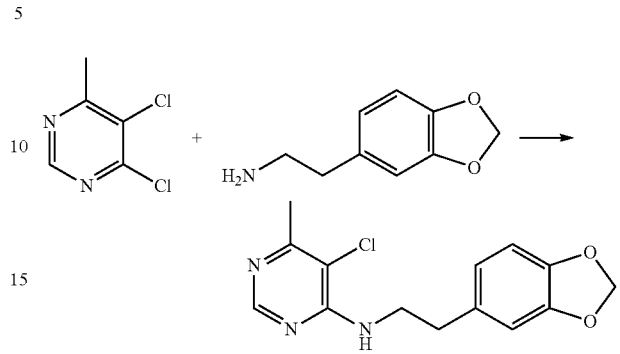

0.21 g (1.5 mmol) of potassium carbonate was added to a solution of 0.16 g (1.0 mmol) of 2-(benzo[d][1,3]dioxol-5-yl)ethanamine in 10 mL of DMF, followed by addition of 0.16 g (1.0 mmol) of 4,5-dichloro-6-methylpyrimidine under stirring, the mixture was heated to 80° C. for 2 h after addition. After the reaction was over by Thin-Layer Chromatography monitoring, the reaction mixture was poured into water and extracted with ethyl acetate, the organic phase was washed with water and saturated brine, dried, filtered and then concentrated under reduced pressure. The residue was purified through silica column (ethyl acetate/petroleum ether (boiling point range 60-90° C.)=1:4, as an eluent) to give 0.23 g of compound 5 as white solid, m.p, 109-110° C.
¹H-NMR (300 MHz, internal standard TMS, solvent CDCl₃) δ (ppm): 2.45 (3H, s), 2.85 (2H, t), 3.71 (2H, q), 5.40 (1H, s), 5.95 (2H, s), 6.72 (3H, m), 8.39 (1H, s).

Example 4

The Preparation of Compound 6

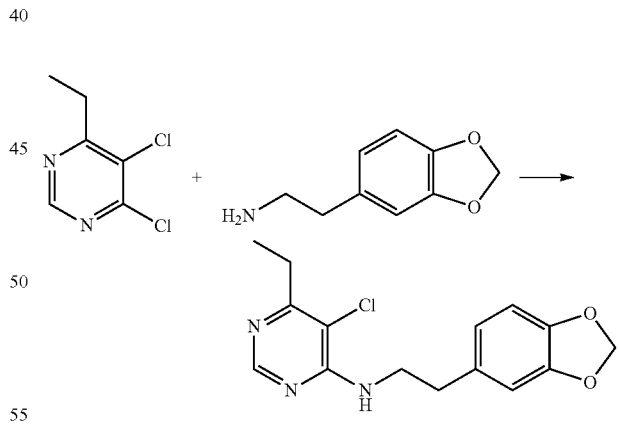

0.21 g (1.5 mmol) of potassium carbonate was added to a solution of 0.16 g (1.0 mmol) of 2-(benzo[d][1,3]dioxol-5-yl)ethanamine in 10 mL of DMF, followed by addition of 0.18 g (1.0 mmol) of 4,5-dichloro-6-ethylpyrimidine (the preparation refers to Example A, the difference is replacing ethyl 2-chloro-3-oxobutanoate to ethyl 2-chloro-3-oxopentanoate) under stirring, the mixture was heated to 80° C. for 2 h after addition. After the reaction was over by Thin-Layer Chromatography monitoring, the reaction mixture was poured into water and extracted with ethyl acetate, the organic phase was washed with water and saturated brine, dried, filtered and then concentrated under reduced pressure. The residue was purified through silica column (ethyl acetate/petroleum ether (boiling point range 60-90° C.)=1:4, as an eluent) to give 0.22 g of compound 6 as white solid, m.p. 116-118° C.

$^1$H-NMR (300 MHz, internal standard TMS, solvent CDCl$_3$) δ (ppm): 1.26 (3H, t), 2.77 (2H, q), 2.84 (2H, t), 3.71 (2H, q), 5.42 (1H, s), 5.95 (2H, s), 6.73 (3H, m), 8.44 (1H, s).

Example 5

The Preparation of Compound 18

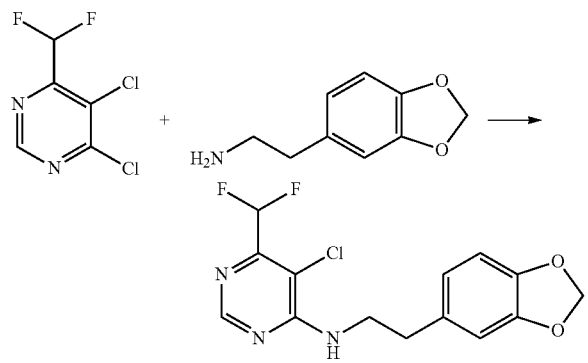

0.21 g (1.5 mmol) of potassium carbonate was added to a solution of 0.16 g (1.0 mmol) of 2-(benzo[d][1,3]dioxol-5-yl)ethanamine in 10 mL of DMF, followed by addition of 0.20 g (1.0 mmol) of 4,5-dichloro-6-(difluoromethyl)pyrimidine under stirring, the mixture was heated to 80° C. for 2 h after addition. After the reaction was over by Thin-Layer Chromatography monitoring, the reaction mixture was poured into water and extracted with ethyl acetate, the organic phase was washed with water and saturated brine, dried, filtered and then concentrated under reduced pressure. The residue was purified through silica column (ethyl acetate/petroleum ether (boiling point range 60-90° C.)=1:4, as an eluent) to give 0.26 g of compound 18 as white solid, m.p. 104-106° C.

$^1$H-NMR (300 MHz, internal standard TMS, solvent CDCl$_3$) δ (ppm): 2.843-2.888 (t, 2H, Ar—CH$_2$), 3.731-3.797 (q, 2H, NH—CH$_2$), 5.65 (s, 1H, NH), 5.950 (s, 1H, O—CH$_2$—O), 6.652-6.784 (m, 3H, Ar—H), 6.667-7.022 (1H, F$_2$C—H), 8.560 (s, 1H, pyrimidine-H).

Example 6

The Preparation of Compound 20

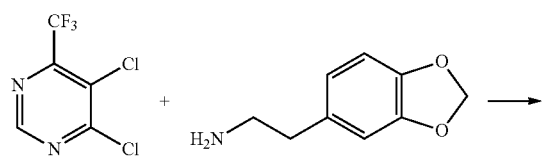

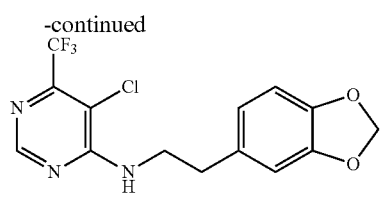

0.21 g (1.5 mmol) of potassium carbonate was added to a solution of 0.16 g (1.0 mmol) of 2-(benzo[d][1,3]dioxol-5-yl)ethanamine in 10 mL of DMF, followed by addition of 0.22 g (1.0 mmol) of 4,5-dichloro-6-(trifluoromethyl)pyrimidine (the preparation refers to Example 2, the difference is replacing ethyl 2-chloro-4,4-difluoro-3-oxobutanoate to ethyl 2-chloro-4,4,4-trifluoro-3-oxobutanoate) under stirring, the mixture was heated to 80° C. for 2 h after addition. After the reaction was over by Thin-Layer Chromatography monitoring, the reaction mixture was poured into water and extracted with ethyl acetate, the organic phase was washed with water and saturated brine, dried, filtered and then concentrated under reduced pressure. The residue was purified through silica column (ethyl acetate/petroleum ether (boiling point range 60-90° C.)=1:4, as an eluent) to give 0.27 g of compound 20 as white solid, m.p. 99-101° C.

$^1$H-NMR (300 MHz, internal standard TMS, solvent CDCl$_3$) δ (ppm): 2.850-2.896 (t, 2H, Ar—CH$_2$), 3.742-3.808 (q, 2H, NH—CH$_2$), 5.65 (s, 1H, NH), 5.959 (s, 1H, O—CH$_2$—O), 6.658-6.792 (m, 3H, Ar—H), 8.564 (s, 1H, pyrimidine-H).

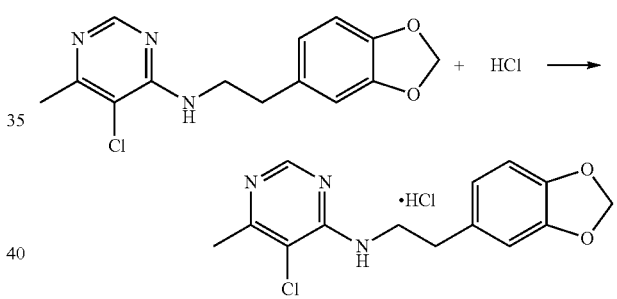

0.44 g (0.015 mol) of compound 5 was dissolved in 20 ml of ethanol, 10 ml of c.HCl was added, the mixture was refluxed for 4-10 h after addition. After the reaction was over by Thin-Layer Chromatography monitoring, the reaction mixture was concentrated under reduced pressure. The brown residue was washed with acetone (3×10 mL) to obtain 0.36 g of compound 1451 as white solid, yield 72.0%, m.p. 199-200° C.

$^1$H-NMR (300 MHz, internal standard TMS, solvent CDCl$_3$) δ (ppm): 2.53 (3H, s), 2.82 (2H, t), 3.71 (2H, m), 5.95 (2H, s), 6.65 (1H, m), 6.76 (2H, m), 8.39 (1H, s).

Other compounds of the present invention were prepared according to the above examples.

Physical properties and $^1$HNMR spectrum ($^1$HNMR, 300 MHz, internal standard: TMS, ppm) of some compounds of this invention are as follows:

Compound 2: m.p. 138-140° C. δ ppm: 2.85 (t 2H), 3.73 (q, 2H), 5.95 (s, 2H), 6.71 (m, 3H), 8.29 (s, 1H).

Compound 104: brown oil. δ ppm: 2.864 (2H, s), 3.73-3.79 (2H, m), 3.96 (3H, s), 5.68 (1H, bs), 5.96 (2H, s), 6.65 (1H, d), 6.71 (1H, s), 6.77 (1H, d).

Compound 1452: m.p. 183-185° C. δ (CDCl$_3$): 2.30 (3H, s), 2.48 (3H, s), 2.81 (2H, m), 3.71 (2H, m), 5.94 (2H, s), 6.66 (1H, m), 6.77 (2H, m), 7.10 (2H, d), 7.48 (2H, d), 8.75 (1H, s), 9.14 (2H, s).

Compound 1465: m.p. 206-208° C. δ (CDCl₃): 1.21 (3H, t), 2.30 (3H, s), 2.76-2.83 (4H, m), 3.70 (2H, m), 5.96 (2H, s), 6.64 (1H, d), 6.78-6.80 (2H, m), 7.10 (2H, d), 7.46 (2H, d), 8.75 (1H, bs), 8.74 (1H, s), 9.02 (1H, bs).

Biological Testing

The compounds of the present invention exhibit both excellent fungicidal activity against many fungi in agricultural field and better insecticidal activity. According to the prior art, the following compounds CK1-CK13 (wherein CK1-3, 5-13 are all unknown compounds, CK4 was disclosed in JP2006008542A and JP2004238380A) and PC-1, ACTA-1 were prepared as controls, they are listed in Table 27.

TABLE 27

The contrast compound list

| No. | Structure |
|---|---|
| CK1 | |
| CK2 | |
| CK3 | |
| CK4 | |
| CK5 | |
| CK6 | |
| CK7 | |
| CK8 | 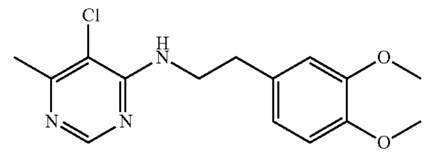 |
| CK9 | 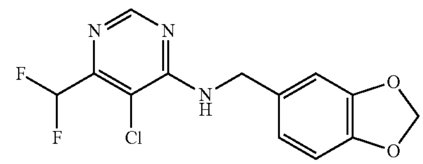 [SMILES: FC(F)c1ncnc(NCc2ccc3c(c2)OCO3)c1Cl] |
| CK10 | 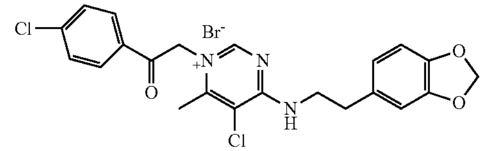 [SMILES: Cc1c(Cl)c(NCCc2ccc3c(c2)OCO3)nc[n+]1CC(=O)c1ccc(Cl)cc1 ; [Br-]] |
| CK11 | 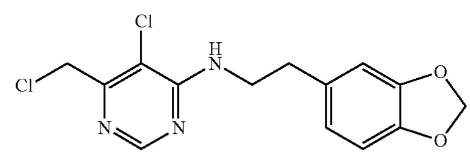 [SMILES: ClCc1ncnc(NCCc2ccc3c(c2)OCO3)c1Cl] |
| CK12 | 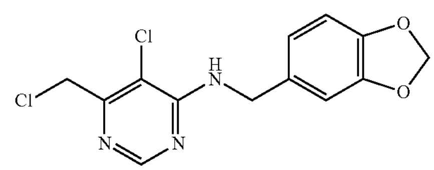 [SMILES: ClCc1ncnc(NCc2ccc3c(c2)OCO3)c1Cl] |
| CK13 | 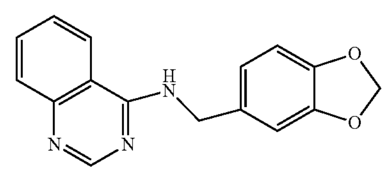 [SMILES: c1ccc2c(NCc3ccc4c(c3)OCO4)ncnc2c1] |
| PC-1 | 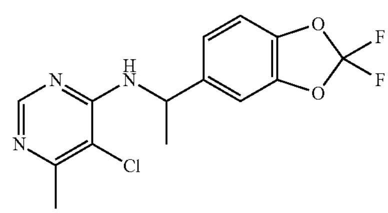 [SMILES: Cc1ncnc(NC(C)c2ccc3c(c2)OC(F)(F)O3)c1Cl] |
| ACTA-1 | 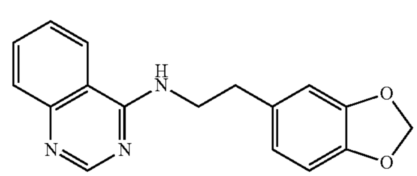 [SMILES: c1ccc2c(NCCc3ccc4c(c3)OCO4)ncnc2c1] |

Example 8

Fungicidal Testing

Determination of fungicidal activity in vitro and protectant activity in vivo of the compounds of the present invention were carried out against many diseases. The fungicidal results are shown in the following examples.

(1) Determination of Fungicidal Activity in Vitro

The method is as followed: High Through Put is used in the test. The compound is dissolved in a proper solvent to become a testing solution whose concentration is designed. The solvent is selected from acetone, methanol, DMF and so on according to their dissolving capability to the sample. In a no animalcule condition, the testing solution and pathogens suspension are added into the cells of 96 cells culture board, which then should be placed in the constant temperature box. 24 hours later, pathogen germination or growth can be investigated by eyeballing, and the activity in vitro of the compound is evaluated based on germination or growth of control treatment.

The activities in vitro (inhibition rate) of some compounds are as follows:

The inhibition rate against rice blast:

At the dose of 25 mg/L, the inhibition rate of compounds 2, 18 was 100%; compound 5 was 80%; contrast compound CK1, CK2, CK4, CK5, CK6, CK7, CK9, CK10, CK13 was all 0, CK8 was 50%;

At the dose of 8.3 mg/L, the inhibition rate of compounds 2, 18 was 100%; PC-1 was 0;

At the dose of 2.8 mg/L, the inhibition rate of compounds 2, 18 was 80%;

At the dose of 0.9 mg/L, the inhibition rate of compound 18 was 80%.

The inhibition rate against cucumber gray mold:

At the dose of 25 mg/L, the inhibition rate of compound 6 was 80%; contrast compounds CK3, CK4, CK7, CK8, CK10, CK13 was all 0; CK11, PC-1, ACTA-1 was all 50%.

(2) The Determination of Protectant Activity in Vivo

The method is as followed: The whole plant is used in this test. The compound is dissolved in a proper solvent to get mother solution. The proper solvent is selected from acetone, methanol, DMF and so on according to their dissolving capability to the sample. The volume rate of solvent and testing solution (v/v) is equal to or less than 5%. The mother solution is diluted with water containing 0.1% tween-80 to get the testing solution whose concentration is designed. The testing solution is sprayed to the host plant by a special plant sprayer. The plant is inoculated with fungus after 24 hours. According to the infecting characteristic of fungus, the plant is stored in a humidity chamber and then transferred into greenhouse after infection is finished. And the other plants are placed in greenhouse directly. The activity of compound is obtained by eyeballing after 7 days in common.

The protectant activities in vivo of some compounds are as follows:

The protectant activity against cucumber downy mildew in vivo:

At the dose of 400 mg/L, the protectant activity of compounds 2, 5, 18, 20, 1451 and so on was 100%, compound 104 was 98%, compound 1452 was 95%;

At the dose of 100 mg/L, the protectant activity of compounds 2, 5, 18, 20 was 100%, compound 104 was 95%;

At the dose of 50 mg/L, the protectant activity of compounds 2, 5, 18, 20 was 100%;

At the dose of 25 mg/L, the protectant activity of compounds 2, 5, 18 was 100%;

At the dose of 12.5 mg/L, the protectant activity of compound 5 was 100%, compound 18 was 80%.

The protectant activity against corn rust in vivo:

At the dose of 400 mg/L, the protectant activity of compounds 5, 6, 18, 1465 was 100%; compound 1451 was 80%;

At the dose of 100 mg/L, the protectant activity of compounds 5, 6, 18 was 100%; compound 1465 was 95%;

At the dose of 25 mg/L, the protectant activity of compounds 5, 6 was 100%;

At the dose of 6.25 mg/L, the protectant activity of compound 5 was 100%, compound 18 was 98%; compound 6 was 90%, The protectant activity against wheat powdery mildew in vivo:

At the dose of 400 mg/L, the protectant activity of compounds 2, 5, 6, 18 was 100%;

At the dose of 100 mg/L, the protectant activity of compounds 5, 18 was 100%, compound 6 was 95%;

At the dose of 25 mg/L, the protectant activity of compound 18 was 100%, compound 6 was 90%, compound 5 was 85%;

At the dose of 6.25 mg/L, the protectant activity of compound 18 was 100%, compound 6 was 85%.

(3) The Contrastive Tests Results of Some Compounds and Contrasts

Contrastive tests were carried out between some compounds and contrasts. The test results are listed in table 28-table 30 ("//" in the following tables means no test).

TABLE 28

The protectant activity against cucumber downy mildew

| | The protectant activity (%) | | | |
|---|---|---|---|---|
| Compound No. | 400 mg/L | 100 mg/L | 50 mg /L | 25 mg /L |
| 2 | 100 | 100 | 100 | 100 |
| 5 | 100 | 100 | 100 | 100 |
| 18 | 100 | 100 | 100 | 100 |
| 20 | 100 | 100 | 100 | 20 |
| 104 | 98 | 95 | 50 | 10 |
| 1451 | 100 | 0 | 0 | 0 |
| 1452 | 95 | 0 | 0 | 0 |
| CK1 | 100 | 30 | 20 | 0 |
| CK2 | 100 | 60 | 40 | 0 |
| CK 3 | 0 | // | // | // |
| CK4 | 0 | // | // | // |
| CK6 | 80 | 0 | // | // |
| CK8 | 98 | 45 | 20 | 0 |
| CK9 | 50 | 0 | // | // |
| CK10 | 0 | // | // | // |
| CK11 | 30 | 0 | // | // |
| CK12 | 50 | 0 | // | // |
| CK13 | 0 | // | // | // |

TABLE 29

The protectant activity against wheat powdery mildew

| | The protectant activity (%) | | | |
|---|---|---|---|---|
| Compound No. | 400 mg/L | 100 mg/L | 25 mg /L | 6.25 mg /L |
| 5 | 100 | 100 | 85 | 75 |
| 6 | 100 | 95 | 90 | 85 |
| 18 | 100 | 100 | 100 | 100 |
| CK1 | 0 | // | // | // |
| CK2 | 60 | 60 | 40 | 0 |
| CK 3 | 0 | // | // | // |
| CK4 | 0 | // | // | // |
| CK5 | 100 | 20 | 0 | // |
| CK6 | 85 | 25 | 0 | // |
| CK7 | 80 | 30 | 0 | // |

TABLE 29-continued

The protectant activity against wheat powdery mildew

| Compound No. | The protectant activity (%) | | | |
|---|---|---|---|---|
| | 400 mg/L | 100 mg/L | 25 mg /L | 6.25 mg /L |
| CK8 | 100 | 80 | 10 | 0 |
| CK9 | 70 | 10 | 0 | // |
| CK10 | 0 | // | // | // |
| CK11 | 0 | // | // | // |
| CK12 | 0 | // | // | // |
| CK13 | 0 | // | // | // |
| PC-1 | 100 | 80 | 0 | // |
| ACTA-1 | 0 | // | // | // |

TABLE 30

The protectant activity against corn rust

| Compound No. | The protectant activity (%) | | | |
|---|---|---|---|---|
| | 400 mg/L | 100 mg/L | 25 mg/L | 6.25 mg/L |
| 5 | 100 | 100 | 100 | 100 |
| 6 | 100 | 100 | 100 | 90 |
| 18 | 100 | 100 | 98 | 30 |
| 1465 | 100 | 95 | 50 | 0 |
| CK1 | 70 | 20 | 0 | // |
| CK2 | 75 | 0 | // | // |
| CK3 | 0 | // | // | // |
| CK4 | 0 | // | // | // |
| CK7 | 70 | 0 | // | // |
| CK8 | 100 | 0 | // | // |
| CK9 | 80 | 25 | 0 | 0 |
| CK10 | 0 | // | // | // |
| CK11 | 85 | 35 | 0 | // |
| CK12 | 40 | 0 | // | // |
| CK13 | 40 | 0 | // | // |
| PC-1 | 70 | 20 | 0 | // |
| ACTA-1 | 0 | // | // | // |

Determination of insecticidal activity of compounds of the present invention against a few insects were carried out by the following procedures;

Compounds were dissolved in mixed solvent (acetone:methanol=1:1), and diluted to required concentration with water containing 0.1% of tween 80.

Diamond back moth, armyworm, Green Peach Aphid and carmine spider mite were used as targets and the method of spraying by airbrush was used for determination of insecticidal biassays.

(1) Determination of Insecticidal Activity Against Diamond Back Moth

The method of spraying by airbrush: The cabbage leaves were made into plates of 2 cm diameter by use of punch. A test solution (0.5 ml) was sprayed by airbrush at the pressure of 0.7 kg/cm$^2$ to both sides of every plate. 10 Second instar larvae were put into the petri-dishes after the leaf disc air-dried and 3 replicates were set for each treatment. Then the insects were maintained in observation room (25° C., 60~70% R.H.). Scores were conducted and mortalities were calculated after 72 h.

Part of test results against diamond back moth:

At 600 mg/L, compounds 6, 18, 1465 showed 100% control of the second instar larvae of diamond back moth, compound 1452 showed 80% control; contrast compounds CK3, CK4, CK8, CK9, CK10, CK11, CK12, CK13, PC-1 showed 0 control, CK2 showed 20% control, CK5, ACTA-1 showed 40% control;

At 100 mg/L, compound 6 showed 90% control of the second instar larvae of diamond back moth, contrast compound CK2 showed 5% control, CK5 showed 20% control, CK6 showed 0 control.

(2) Determination of Insecticidal Activity Against Armyworm

The method of spraying by airbrush: The corn leaves were made into plates of 2 cm diameter by use of punch. A test solution (0.5 ml) was sprayed by airbrush at the pressure of 0.7 kg/cm$^2$ to both sides of every plate. 10 Second instar larvae were put into the petri-dishes after the leaf disc air-dried and 3 replicates were set for each treatment. Then the insects were maintained in observation room (25° C., 60~70% R.H.). Scores were conducted and mortalities were calculated after 72 h.

Part of test results against armyworm:

At 600 mg/L, compound 18 showed 100% control of the armyworm, compound 6 showed 90% control; contrast compounds CK1, CK3, CK4, CK5, CK6, CK7, CK8, CK9, CK10, CK11, CK12, CK13, PC-1 showed 0 control, CK2 showed 14% control, ACTA-1 showed 40% control:

At 100 mg/L, compound 6 showed 90% control of the armyworm; contrast compound CK2 showed 0 control.

(3) Determination of Acancidal Activity Against Carmine Spider Mite

Method: Broadbean shoots with two true leaves in pot were taken, the healthy adults of carmine spider mite were inoculated to the leaves. The adults were counted and then sprayed with airbrush at the pressure of 0.7 kg/cm$^2$ and at dose of 0.5 ml. 3 replicates were set for each treatment. And then they were maintained in standard observation room. Scores were conducted and mortalities were calculated after 72 hrs.

Parts of the test results against carmine spider mite are as follows:

At the dose of 100 mg/L, compound 18 showed 90% control against carmine spider mite; Contrast compounds CK2, CK3, CK4, CK5, CK6, CK9, CK10, CK12, CK13, ACTA-1 showed 0 control, PC-1 showed 51% control, CK1 showed 39% control, CK11 showed 25% control.

(4) Determination of Activity Against Green Peach Aphid

Method: Filter papers were put in culture dishes (Diameter=6 cm), and water was dripped on filter papers for preserving moisture. Green peach aphids (*Myzus Persicae* Sulzer) were maintained on cabbage. Leaves (Diameter=3 cm) of approximately 15-30 aphids were put in the culture dishes. Bioactivity tests were used the method of Airbrush Foliar Spray, pressure=10 psi (0.7 kg/cm2), spray volume=0.5 mL. The studies were conducted at three constant temperatures 25±1 C. in incubator cabinets with 60±5% RH. Survey the survival aphids after 48 h and calculate the death rates.

Parts of the test results against green peach aphid are as follows:

At the dose of 600 mg/L, compounds 5, 6, 18, 1451, 1465 showed 100% control against Green Peach Aphid; Compound 1452 showed 90% control;

At the dose of 100 mg/L, compounds 6, 18 showed 100% control.

Contrastive tests were carried out between some compounds and contrasts. The test results are listed in table 31 ("//" in the following tables means no test).

TABLE 31

Contrastive tests of some compounds and contrasts against peach aphid

| Compound No. | Insecticidal activity against peach aphid (%) | | |
|---|---|---|---|
| | 600 mg/L | 100 mg/L | 10 mg/L |
| 5 | 100 | 52 | 0 |
| 6 | 100 | 100 | 100 |
| 18 | 100 | 100 | 68 |
| 1465 | 100 | 70 | 0 |
| CK1 | 70 | 30 | 0 |
| CK2 | 20 | 12 | 0 |
| CK 3 | 0 | // | // |
| CK4 | 0 | // | // |
| CK5 | 100 | 35 | 8 |
| CK6 | 0 | // | // |
| CK7 | 66 | 37 | 0 |
| CK8 | 0 | // | // |
| CK10 | 0 | // | // |
| CK11 | 88 | 0 | 0 |
| CK12 | 10 | 0 | 0 |
| CK13 | 50 | 0 | 0 |
| PC-1 | 52 | 0 | // |
| ACTA-1 | 0 | // | // |

Determination of Antitumor Activity

Example 10

In Vitro Cell Inhibition Assay Against Human Cancer Cell T24 (Bladder Cancer Cell Line)

The tested compounds are dissolved in DMSO and diluted to designed concentration with culture medium.

The of cell culture technology in vitro was selected to evaluate growth inhibition rate against human bladder cancer cell line T24. 1000 to 3000 cells were inoculated into 24-well plate, followed by addition of cell culture medium (1 mL) known for technicans in this field (culture medium is RMPI-1640), after cells were cultured in incubator ($CO_2$ 5%, 37° C.) for 24 hours, then the tested compounds with designed concentration were added to each well. One thing should be paid much attention is that the culture medium volume, of tested compound does not exceed 0.5 of total volume. After incubation for one week, the culture medium was removed, the plate wells were washed with cold PBS once, fixed with 1% formalin at room temperature for 10 minutes, and washed with cold PBS one more time, followed by stain with 0.1% crystal violet for 30 minutes. Crystal violet can be recycled. The stained cells were washed with deionized water gently, dried in the air and reserved, were then incubated for 4 h. The inhibition rate was calculated according to the left cells of each treatment and contrast.

The inhibition rate=the left cells of each treatment/the left cells of contrast×100%

Part of the test results are as follows:

At the dose of 10 μM, the inhibition rate of compounds 5, 6 against bladder cancer cell line T24 was 100%.

We claim:
1. A compound of formula I:

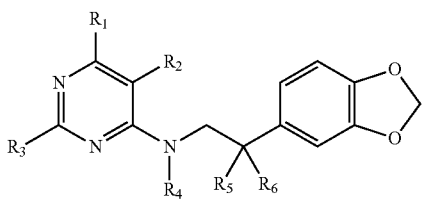

wherein:
$R_1$ is selected from halo, $C_1$-$C_8$alkyl, halo$C_1$-$C_8$alkyl, $C_3$-$C_8$cycloalkyl, $C_1$-$C_8$alkoxy, halo$C_1$-$C_8$alkoxy, $C_3$-$C_8$alkenyloxy, halo$C_3$-$C_8$alkenyloxy, $C_3$-$C_8$alkynyloxy, halo$C_3$-$C_8$alkynyloxy, $C_1$-$C_8$alkylsulfonyloxy, $C_1$-$C_8$alkylthio, $C_1$-$C_8$alkylsulfinyl, $C_1$-$C_8$alkylsulfonyl, $C_1$-$C_8$alkylamino, di($C_1$-$C_8$alkyl)amino, cyano$C_1$-$C_8$alkylamino, $C_1$-$C_8$alkylcarbonylamino, $C_1$-$C_8$alkoxycarbonylamino, $C_1$-$C_8$alkoxy$C_1$-$C_8$alkyl, $C_1$-$C_8$alkylthio$C_1$-$C_8$alkyl, $C_1$-$C_8$alkylsulfinyl$C_1$-$C_8$alkyl, $C_1$-$C_8$alkylsulfonyl$C_1$-$C_8$alkyl, hydroxy$C_1$-$C_8$alkyl or $C_1$-$C_8$alkylcarbonyloxy$C_1$-$C_8$alkyl;
$R_2$ is selected from H, halo, CN, $NO_2$, $C_1$-$C_8$alkyl, $C_1$-$C_8$alkoxy or halo$C_1$-$C_8$alkoxy;
$R_3$ is selected from H, halo or $C_1$-$C_8$alkyl;
$R_4$ is selected from H, OH, C(=O)H, $C_1$-$C_8$alkyl, halo$C_1$-$C_8$alkyl, $C_1$-$C_8$alkoxy, halo$C_1$-$C_8$alkoxy, $C_3$-$C_8$cycloalkyl, $C_1$-$C_8$alkylthio, $C_2$-$C_8$alkenylthio, $C_2$-$C_8$alkenyl, $C_2$-$C_8$alkynyl, halo$C_2$-$C_8$alkenyl, halo$C_2$-$C_8$alkynyl, $C_1$-$C_8$alkoxy$C_1$-$C_8$alkyl, halo$C_1$-$C_8$alkoxy$C_1$-$C_8$alkyl, $C_1$-$C_8$alkylthio$C_1$-$C_8$alkyl, halo$C_1$-$C_8$alkylthio$C_1$-$C_8$alkyl, $C_1$-$C_8$alkylsulfinyl, halo$C_1$-$C_8$alkylsulfinyl, $C_1$-$C_8$alkylsulfonyl, halo$C_1$-$C_8$alkylsulfonyl, $C_1$-$C_8$alkylaminosulfonyl, di($C_1$-$C_8$alkyl)aminosulfonyl,
$C_1$-$C_8$alkylsulfonylaminocarbonyl,
$C_1$-$C_8$alkylcarbonylaminosulfonyl,
$C_3$-$C_8$cycloalkyloxycarbonyl, $C_1$-$C_8$alkylcarbonyl, halo$C_1$-$C_8$alkylcarbonyl, $C_1$-$C_8$alkoxycarbonyl, halo$C_1$-$C_8$alkoxycarbonyl, $C_1$-$C_8$alkylcarbonyl$C_1$-$C_8$alkyl, $C_1$-$C_8$alkoxycarbonyl$C_1$-$C_8$alkyl, $C_1$-$C_8$alkylaminocarbonyl, di($C_1$-$C_8$alkyl)aminocarbonyl, $C_2$-$C_8$alkenoxycarbonyl, $C_2$-$C_8$alkynoxycarbonyl, $C_1$-$C_8$alkoxy$C_1$-$C_8$alkoxycarbonyl,
$C_1$-$C_8$alkylaminothio, di($C_1$-$C_8$alkyl)aminothio, optionally substituted arylcarbonyl$C_1$-$C_6$alkyl, arylcarbonyl, aryloxycarbonyl, aryl$C_1$-$C_6$alkoxycarbonyl, aryl$C_1$-$C_6$alkyl or heteroaryl$C_1$-$C_6$alkyl, wherein substituents are independently selected from the group consisting of halo, $NO_2$, CN, $C_1$-$C_6$alkyl, halo$C_1$-$C_6$alkyl, $C_1$-$C_4$alkoxy and halo$C_1$-$C_4$alkoxy; and
$R_5$ and $R_6$ are independently selected from H, $C_1$-$C_8$alkyl, $C_3$-$C_8$cycloalkyl, $C_2$-$C_8$alkenyl, $C_2$-$C_8$alkynyl, halo$C_2$-$C_8$alkenyl, halo$C_2$-$C_8$alkynyl, $C_1$-$C_8$alkoxy$C_1$-$C_8$alkyl, optionally substituted aryl$C_1$-$C_4$alkyl or heteroaryl$C_1$-$C_4$alkyl, wherein substituents are independently selected from the group consisting of halo, $C_1$-$C_4$alkyl, halo$C_1$-$C_4$alkyl, $C_1$-$C_4$alkoxy and halo$C_1$-$C_4$alkoxy;
or $R_5$ and $R_6$, together with the carbon to which they are attached, form a $C_3$-$C_8$carbocycle;
or an agricultural or pharmaceutical salt thereof.

2. The compound according to claim 1, wherein:

$R_1$ is selected from halo, $C_1$-$C_4$alkyl, halo$C_1$-$C_4$alkyl, $C_3$-$C_6$cycloalkyl, $C_1$-$C_4$alkoxy, halo$C_1$-$C_4$alkoxy, $C_3$-$C_6$alkenyloxy, halo$C_3$-$C_6$alkenyloxy, $C_3$-$C_6$alkynyloxy, halo$C_3$-$C_6$alkynyloxy, $C_1$-$C_4$alkylsulfonyloxy, $C_1$-$C_4$alkylthio, $C_1$-$C_4$alkylsulfinyl, $C_1$-$C_4$alkylsulfonyl, $C_1$-$C_4$alkylamino, di($C_1$-$C_4$alkyl)amino, cyano$C_1$-$C_4$alkylamino, $C_1$-$C_4$alkylcarbonylamino, $C_1$-$C_4$alkoxycarbonylamino, $C_1$-$C_4$alkoxy$C_1$-$C_4$alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl, hydroxy$C_1$-$C_4$alkyl or $C_1$-$C_4$alkylcarbonyloxy$C_1$-$C_4$alkyl;

$R_2$ is selected from H, halo, CN, $NO_2$, $C_1$-$C_4$alkyl, $C_1$-$C_4$alkoxy or halo$C_1$-$C_4$alkoxy;

$R_3$ is H;

$R_4$ is selected from H, OH, C(=O)H, $C_1$-$C_4$alkyl, halo$C_1$-$C_4$alkyl, $C_1$-$C_4$alkoxy, halo$C_1$-$C_4$alkoxy, $C_3$-$C_6$cycloalkyl, $C_1$-$C_4$alkylthio, $C_2$-$C_4$alkenylthio, $C_2$-$C_4$alkenyl, $C_2$-$C_4$alkynyl, halo$C_2$-$C_4$alkenyl, halo$C_2$-$C_4$alkynyl, $C_1$-$C_4$alkoxy$C_1$-$C_4$alkyl, halo$C_1$-$C_4$alkoxy$C_1$-$C_4$alkyl, $C_1$-$C_4$alkylthio$C_1$-$C_4$alkyl, halo$C_1$-$C_4$alkylthio$C_1$-$C_4$alkyl, $C_1$-$C_4$alkylsulfinyl, halo$C_1$-$C_4$alkylsulfinyl, $C_1$-$C_4$alkylsulfonyl, halo$C_1$-$C_4$alkylsulfonyl, $C_1$-$C_4$alkylaminosulfonyl, di($C_1$-$C_4$alkyl)aminosulfonyl, $C_1$-$C_4$alkylsulfonylaminocarbonyl, $C_1$-$C_4$alkylcarbonylaminosulfonyl, $C_3$-$C_6$cycloalkyloxycarbonyl, $C_1$-$C_4$alkylcarbonyl, halo$C_1$-$C_4$alkylcarbonyl, $C_1$-$C_4$alkoxycarbonyl, halo$C_1$-$C_4$alkoxycarbonyl, $C_1$-$C_4$alkylcarbonyl$C_1$-$C_4$alkyl, $C_1$-$C_8$alkoxycarbonyl$C_1$-$C_4$alkyl, $C_1$-$C_4$alkylaminocarbonyl, di($C_1$-$C_4$alkyl)aminocarbonyl, $C_2$-$C_4$alkenoxycarbonyl, $C_2$-$C_4$alkynoxycarbonyl, $C_1$-$C_4$alkoxy$C_1$-$C_4$alkoxycarbonyl, $C_1$-$C_4$alkylaminothio, di($C_1$-$C_4$alkyl)aminothio, optionally substituted arylcarbonyl$C_1$-$C_4$alkyl, arylcarbonyl, aryloxycarbonyl, aryl$C_1$-$C_4$alkoxycarbonyl, aryl$C_1$-$C_4$alkyl or heteroaryl$C_1$-$C_4$alkyl, wherein substituents are independently selected from the group consisting of halo, $NO_2$, CN, $C_1$-$C_4$alkyl, halo$C_1$-$C_4$alkyl, $C_1$-$C_4$alkoxy and halo$C_1$-$C_4$alkoxy; and $R_5$ and $R_6$ are independently selected from H, $C_1$-$C_4$alkyl, $C_3$-$C_6$cycloalkyl, $C_2$-$C_4$alkenyl, $C_2$-$C_4$alkynyl, halo$C_2$-$C_4$alkenyl, halo$C_2$-$C_4$alkynyl, $C_1$-$C_4$alkoxy$C_1$-$C_4$alkyl, optionally substituted aryl$C_1$-$C_4$alkyl or heteroaryl$C_1$-$C_4$alkyl, wherein substituents are independently selected from the group consisting of halo, $C_1$-$C_4$alkyl, halo$C_1$-$C_4$alkyl, $C_1$-$C_4$alkoxy and halo$C_1$-$C_4$alkoxy;

or $R_5$ and $R_6$, together with the carbon to which they are attached, form a $C_3$-$C_8$carbocycle;

or an agricultural or pharmaceutical salt thereof selected from the group consisting of hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid and citric acid.

3. The compound according to claim 2, wherein:

$R_1$ is selected from halo, $C_1$-$C_4$alkyl, $CF_3$, $CHF_2$, $CCl_3$, $CHCl_2$, $C_3$-$C_6$cycloalkyl, $C_1$-$C_4$alkoxy, halo$C_1$-$C_4$alkoxy, $C_1$-$C_4$alkylthio, $C_1$-$C_4$alkylsulfinyl, $C_1$-$C_4$alkylsulfonyl, $C_1$-$C_4$alkoxy$C_1$-$C_4$alkyl or $C_1$-$C_4$alkylthio$C_1$-$C_4$alkyl;

$R_2$ is selected from H, halo, CN, $NO_2$, $C_1$-$C_4$alkyl, $C_1$-$C_4$alkoxy or halo$C_1$-$C_4$alkoxy;

$R_3$ is H;

$R_4$ is selected from H, OH, C(=O)H, $C_1$-$C_4$alkyl, $C_3$-$C_6$cycloalkyl, optionally substituted arylcarbonyl$C_1$-$C_4$alkyl, arylcarbonyl, aryloxycarbonyl, aryl$C_1$-$C_4$alkoxycarbonyl, aryl$C_1$-$C_4$alkyl or heteroaryl$C_1$-$C_4$alkyl, wherein substituents are independently selected from the group consisting of halo, $NO_2$, CN, $C_1$-$C_4$alkyl, halo$C_1$-$C_4$alkyl, $C_1$-$C_4$alkoxy and halo$C_1$-$C_4$alkoxy; and $R_5$ and $R_6$ are independently selected from H or $C_1$-$C_4$alkyl;

or an agricultural or pharmaceutical salt thereof selected from the group consisting of hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid and citric acid.

4. The compound according to claim 3, wherein:

$R_1$ is selected from halo, $C_1$-$C_4$alkyl, $CF_3$, $CHF_2$ or $C_3$-$C_6$cycloalkyl;

$R_2$ is selected from H, halo, CN, $NO_2$ or $C_1$-$C_4$alkyl;

$R_3$ is H;

$R_4$ is H; and $R_5$ and $R_6$ are independently selected from H, $CH_3$ or $CH_2CH_3$;

or an agricultural or pharmaceutical salt thereof selected from the group consisting of hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid and citric acid.

5. The compound according to claim 4, wherein:

$R_1$ is selected from F, Cl, Br, $CH_3$, $CH_2CH_3$, $(CH_2)_2CH_3$, $CH(CH_3)_2$, $(CH_2)_3CH_3$, $CH_2CH(CH_3)_2$, $C(CH_3)_3$, $CF_3$, $CHF_2$ or cyclopropyl;

$R_2$ is Cl;

$R_3$ is H;

$R_4$ is H; and $R_5$ and $R_6$ are independently selected from H, $CH_3$ or $CH_2CH_3$;

or an agricultural or pharmaceutical salt thereof selected from the group consisting of hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid and citric acid.

6. The compound according to claim 5, wherein:

$R_1$ is selected from Cl, $CH_3$, $CH_2CH_3$, $CF_3$ or $CHF_2$;

$R_2$ is Cl;

$R_3$ is H;

$R_4$ is H;

$R_5$ is H; and $R_6$ is H;

or an agricultural or pharmaceutical salt thereof selected from the group consisting of hydrochloric acid, sulfuric acid, phosphoric acid, trifluoroacetic acid, methylsulfonic acid and p-toluenesulfonic acid.

7. A composition comprising a compound according to claim 1 as an active ingredient and an agriculturally acceptable carrier.

8. A method of treating a fungal condition in a subject, comprising administering to said subject an effective amount of a compound according to claim 1.

9. A method of treating crops, comprising contacting said crops with an effective amount of a compound according to claim 1.

10. A method for treating tumors in a subject, comprising administering to said subject an effective amount of a compound according to claim 1.

11. A method for the preparation of a compound of formula I according to claim 1, comprising:

reacting a compound of formula II:

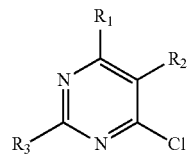

wherein $R_1$, $R_2$ and $R_3$ are as defined in claim 1; with a compound of formula III:

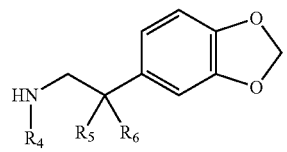

wherein $R_4$, $R_5$ and $R_6$ are as defined in claim 1; to provide a compound of formula I:

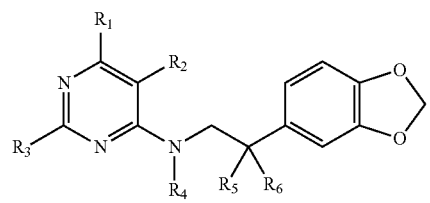

wherein $R_1$, $R_2$, $R_3$, $R_4$, $R_5$ and $R_6$ are as defined in claim 1.

* * * * *